United States Patent
Gabizon et al.

(10) Patent No.: US 10,080,807 B2
(45) Date of Patent: Sep. 25, 2018

(54) COMBINATION CHEMOTHERAPY COMPRISING A LIPOSOMAL PRODRUG OF MITOMYCIN C

(71) Applicants: LIPOMEDIX PHARMACEUTICALS LTD., Jerusalem (IL); SHAARE ZEDEK SCIENTIFIC LTD., Jerusalem (IL)

(72) Inventors: Alberto Gabizon, Jerusalem (IL); Patricia Ohana, Jerusalem (IL); Hilary Shmeeda, Givat Zev (IL)

(73) Assignees: Lipomedix Pharmaceuticals Ltd., Jerusalem (IL); Shaare Zedek Scientific Ltd., Jerusalem (IL)

( * ) Notice: Subject to any disclaimer, the term of this patent is extended or adjusted under 35 U.S.C. 154(b) by 6 days.

(21) Appl. No.: 15/317,779

(22) PCT Filed: Jun. 9, 2015

(86) PCT No.: PCT/US2015/034876
§ 371 (c)(1),
(2) Date: Dec. 9, 2016

(87) PCT Pub. No.: WO2015/191563
PCT Pub. Date: Dec. 17, 2015

(65) Prior Publication Data
US 2017/0112807 A1 Apr. 27, 2017

Related U.S. Application Data

(60) Provisional application No. 62/120,637, filed on Feb. 25, 2015, provisional application No. 62/009,767, filed on Jun. 9, 2014.

(51) Int. Cl.
*A61K 31/337* (2006.01)
*A61K 47/54* (2017.01)
(Continued)

(52) U.S. Cl.
CPC .......... *A61K 47/543* (2017.08); *A61K 9/0019* (2013.01); *A61K 9/0053* (2013.01);
(Continued)

(58) Field of Classification Search
CPC .................................................... A61K 31/337
See application file for complete search history.

(56) References Cited

U.S. PATENT DOCUMENTS 6,365,179 B1 * 4/2002 Zalipsky .............. A61K 9/0019
  205/254
6,787,132 B1   9/2004 Gabizon et al.
(Continued)

FOREIGN PATENT DOCUMENTS

WO   WO 2015/191563 A1   12/2015
WO   WO 2015/191576 A1   12/2015

OTHER PUBLICATIONS

Chen et al., "No survival benefit from postoperative adjuvant chemotherapy after D2 radical resection for the patients with stage II gastric cancer", Am. J. Clin. Oncol., vol. 34, No. 3, pp. 309-313 (2011).
(Continued)

*Primary Examiner* — Benjamin J Packard
(74) *Attorney, Agent, or Firm* — McDermott Will & Emery LLP

(57) ABSTRACT

The present invention is based on a finding of an unexpected synergistic and safe combination of antineoplastic agents which when administered in combination provides greater efficacy than the single agents alone. Accordingly, a method of treating neoplasia in a subject in need of treatment is provided, by administering to the subject an amount of a prodrug of mitomycin C that yields a therapeutically effective amount of mitomycin C, in combination with an amount of a chemotherapeutic agent. In one embodiment, the pro-
(Continued)

drug of mitomycin C is a liposomal-prodrug of mitomycin C. Together, the prodrug of mitomycin C and chemotherapeutic agent provide a synergistic antineoplastic effect.

22 Claims, 13 Drawing Sheets

(51) Int. Cl.
  *A61K 9/127*   (2006.01)
  *A61K 45/06*   (2006.01)
  *A61K 31/407*   (2006.01)
  *A61K 31/513*   (2006.01)
  *A61K 31/704*   (2006.01)
  *A61K 31/7068*   (2006.01)
  *A61K 9/00*   (2006.01)
  *A61K 47/69*   (2017.01)

(52) U.S. Cl.
  CPC ............ *A61K 9/127* (2013.01); *A61K 31/337* (2013.01); *A61K 31/407* (2013.01); *A61K 31/513* (2013.01); *A61K 31/704* (2013.01); *A61K 31/7068* (2013.01); *A61K 45/06* (2013.01); *A61K 47/6911* (2017.08)

(56) References Cited

U.S. PATENT DOCUMENTS

| | | | |
|---|---|---|---|
| 6,984,396 | B2 | 1/2006 | Zalipsky et al. |
| 7,303,760 | B2 | 12/2007 | Zalipsky et al. |
| 2004/0013660 | A1 | 1/2004 | Bissery |
| 2004/0161455 | A1* | 8/2004 | Zalipsky ............... A61K 31/407 424/450 |
| 2009/0131367 | A1 | 5/2009 | Gore et al. |
| 2017/0119895 | A1 | 5/2017 | Gabizon et al. |

OTHER PUBLICATIONS

Cheung et al., "In vivo efficacy and toxicity of intratumorally delivered mitomycin C and its combination with doxorubicin using microsphere formulations", Anti-Cancer Drugs, vol. 16, No. 4, pp. 423-433 (2005).
Cheung et al., "In vitro toxicity to breast cancer cells of microsphere-delivered mitomycin C and its combination with doxorubicin", Eur. J. Pharm. Biopharm., vol. 62, No. 3, pp. 321-331 (2006).
Gabizon et al., "Reduced Toxicity and Superior Therapeutic Activity of aMitomycin CLipid-Based Prodrug Incorporated in Pegylated Liposomes", Clinical Cancer Research, vol. 12, No. 6, pp. 1913-1920 (2006).
Galanis et al., "Phase I-II trial of ONYX-015 in combination with MAP chemotherapy in patients with advanced sarcomas", Gene Ther., vol. 12, No. 5, pp. 437-445 (2005).
Ghanaati et al., "Efficacy of transarterial chemoembolization on lesion reduction in colorectal liver metastases", Acta. Med. Iran., vol. 50, No. 8, pp. 535-540 (2012).
Gibson et al.., "Phase II study of 5-fluorouracil, doxorubicin, and mitomycin C for metastatic small bowel adenocarcinoma", Oncologist, vol. 10, No. 2, pp. 132-137 (2005).
Gnad-Volt et al., "Pegylated liposomal doxorubicin and mitomycin C in combination with infusional 5-fluorouracil and sodium folinic acid in the treatment of advanced gastric cancer: results of a phase II trial", Anticancer Drugs, vol. 16, No. 4, pp. 435-440 (2005).
Hofheinz et al., "Treatment of a patient with advanced esophageal cancer with a combination of mitomycin C and capecitabine: activation of the thymidine phosphorylase as active principle?", Onkologie, vol. 26, No. 2, pp. 161-164 (2003).

International Search Report from PCT Patent Application No. PCT/US2015/034876 dated Aug. 24, 2015, application now published as International Publication No. WO2015/191563 dated Dec. 17, 2015.
International Search Report from PCT Patent Application No. PCT/US2015/034897 dated Aug. 24, 2015, application now published as International Publication No. WO2015/191576 dated Dec. 17, 2015.
Kawano et al., "Synergistic antitumor activity of interleukin-2, mitomycin C and 5-fluorouracil against colon cancer", Proc. Am. Assoc. Cancer Res., vol. 35, No. 0, p. 323, Abst. 1920 (1994).
Kornek et al., "Combined radiochemotherapy of locally advanced unresectable pancreatic adenocarcinoma with mitomycin C plus 24-hour continuous infusional gemcitabine", Int. J. Radiat. Oncol. Biol. Phys., vol. 49, No. 3, pp. 665-671 (2001).
Kostkova et al., "HPMA copolymer conjugates of DOX and mitomycin C for combination therapy: physicochemical characterization, cytotoxic effects, combination index analysis, and anti-tumor efficacy", Macromol. Biosci., vol. 13, No. 2, pp. 1648-1660 (2013).
Lee et al., "Second-line treatment with a combination of continuous 5-fluorouracil, doxorubicin, and mitomycin-C (conti-FAM) in gemcitabine-pretreated pancreatic and biliary tract cancer", Am. J. Clin. Oncol., vol. 32, No. 4, pp. 348-352 (2009).
Lewis et al., "Mitomycin C (MMC) combined with paclitaxel (PCTX)—A clinical and pharmacokinetic study", Clinical Pharmacology and Therapeutics, vol. 65, No. 2, p. 198, Abst. PIII-89 (1999).
Ludgate et al., "Synchronous 5-fluorouracil, mitomycin-C and radiation therapy in the treatment of locally advanced carcinoma of the cervix", Int. J. Rad. Oncol. Biol. Phys., vol. 15, No. 4, pp. 893-899 (1988).
Misra et al., "Intrahepatic arterial infusion with combination of Mitomycin C (MMC) and 5-Flurouracil (5-FU) for treatment of Primary and Metastatic Carcinoma of Liver", Reg. Cancer Treat, vol. 1-2, pp. 12-16 (1992).
Opyrchal et al., "Phase I clinical trial of locoregional administration of the oncolytic adenovirus ONYX-015 in combination with mitomycin-C, doxorubicin and cisplatin chemotherapy in patients with advanced sarcomas", Methods Mol, Biol., vol. 542, pp. 705-717 (2009).
Patterson et al., "Prodrugs in genetic chemoradiotherapy", Curr. Pharm. Des., vol. 9, No. 26, pp. 2131-2154 (2003).
Peters et al., "Synergism of gemcitabine (GEM) with etoposide (VP), mitomycine C (MMC) and LY231514 (LY)", Proc. Amer. Cancer Res., vol. 38, No. 0, p. 319, Abst. 2136 (1997).
Prasad et al., "Doxorubicin and mitomycin C co-loaded polymer-lipid hybrid nanoparticles inhibit growth of sensitive and multidrug resistant human mammary tumor xenografts", Cancer Letters, vol. 334, No. 2, pp. 263-273 (2013).
Rockwell, "Combination therapy with radiation, mitomycin C, and 5-fluorouracil in EMT6 tumors", Int. J. Radiation Oncology Biol. Phys., vol. 28, No. 1, pp. 127-133 (1994).
Saif et. al., "S-1: a promising new oral fluoropyrimidine derivative", Expert Opin. Investig. Drugs, vol. 18, No. 3, pp. 335-348 (2009).
Shuhendler et al., "On the synergistic effect of doxorubicin and mitomycin C against breast cancer cells", Drug Metabol. Drug Interact., vol. 22, No. 4, pp. 201-233 (2007).
Shuhendler et al., "A novel doxorubicin-mitomycin C co-encapsulated nanoparticle formulation exhibits anti-cancer synergy in multidrug resistant human breast cancer cells", Breast Cacner Res. Treat, vol. 119, No. 2, pp. 255-269 (2009).
Toyama et al., "A case of postoperative liver metastasis from pancreatic carcinoma treated with percutaneous isolated hepatic perfusion(PIHP)", Gan To Kagaku Ryoho, vol. 39, No. 12, pp. 1886-1888 (2012) English Abstract.
Yonemoto et al., "A multi-center retrospective analysis of survival benefits of chemotherapy for unresectable biliary tract cancer", Jpn. J. Clin. Oncol., vol. 37, No. 11, pp. 843-851 (2007).

\* cited by examiner

COMBINATION CHEMOTHERAPY COMPRISING A LIPOSOMAL PRODRUG OF MITOMYCIN C

CROSS-REFERENCE TO RELATED APPLICATIONS

This application is a U.S. National Stage of International Patent Application No. PCT/US2015/034876, filed Jun. 9, 2015, which claims the benefit of U.S. Provisional Application No. 62/009,767, filed Jun. 9, 2014, and of U.S. Provisional Application No. 62/120,637, filed Feb. 25, 2015, each of which is incorporated by reference herein in its entirety.

TECHNICAL FIELD

The subject matter described herein relates to methods for treating patients in need of treatment for a neoplastic condition by a combination of a liposomal prodrug of mitomycin C and a chemotherapeutic agent.

BACKGROUND

Cancer is a leading cause of death in the United States and affects people worldwide. Surgery, radiation and chemotherapy are the most widely used therapeutic modalities. Chemotherapy agents create conditions within the cell that limit cell growth and replication, and cancer chemotherapy has advanced dramatically in recent years. Chemotherapy agents typically affect both neoplastic and rapidly proliferating cells of normal tissue such as bone marrow, hair follicles and intestinal epithelium. Anorexia, nausea, vomiting, diarrhea, suppression of bone marrow function and hair loss are some of the negative effects commonly associated with chemotherapy. Development of a chemotherapy agent and unique combinations of agents that provide effective antitumor therapy with minimal toxicity would be advantageous.

BRIEF SUMMARY

The following aspects and embodiments thereof described and illustrated below are meant to be exemplary and illustrative, not limiting in scope.

In one aspect, a method of treatment is provided. The method comprises providing to a subject in need a prodrug of mitomycin C in an amount that yields a therapeutically-effective amount of mitomycin C; and instructing to administer, or administering, in combination with the prodrug a chemotherapeutic agent.

In one embodiment, the prodrug is a conjugate of mitomycin C releasably attached to a lipophilic moiety.

In another embodiment, providing a prodrug of mitomycin C comprises providing via injection a prodrug of mitomycin C.

In yet another embodiment, providing via injection comprises intravenous, intraarterial, intraperitoneal, intrapleural, intrathecal, intravesical or intratumoral injection.

In still another embodiment, instructing comprises instructing to administer the chemotherapeutic agent concurrently or sequentially with the prodrug.

In one embodiment, the chemotherapeutic agent is a liposome-entrapped chemotherapeutic agent. In an exemplary embodiment, the chemotherapeutic agent is doxorubicin or daunorubicin. In another exemplary embodiment, the chemotherapeutic agent is a taxane, including but not limited to paclitaxel and docetaxel. In still another exemplary embodiment, the chemotherapeutic agent is gemcitabine or a fluoropyrimidine, such as but not limited to 5-fluorouracil or a prodrug of 5-fluorouracil. Exemplary prodrugs of 5-fluorouracil include S-1 and capecitabine.

In one embodiment, instructing comprises instructing to administer the chemotherapeutic agent orally.

In another aspect, a treatment regimen for a subject with a neoplasm (e.g., cancer) comprises administering a prodrug of mitomycin C in an amount that yields a therapeutically-effective amount of mitomycin C; and administering a chemotherapeutic agent that is not the prodrug or mitomycin C as a free agent. The combined therapy provides a reduction in tumor volume or a prolongation in survival of the subject, when compared to that achieved by administering the prodrug or the chemotherapeutic agent alone.

In one embodiment, the neoplasm in the patient is a cancer such as breast cancer, melanoma, colon cancer, colorectal cancer, stomach cancer, esophageal cancer, pancreatic cancer, or bladder cancer.

In yet another aspect, a method for treating a solid tumor is provided. The method comprises providing a prodrug of mitomycin C in an amount that yields a therapeutically-effective amount of mitomycin C; and providing instructions to administer in combination with the prodrug a chemotherapeutic agent.

In one embodiment, the chemotherapeutic agent co-administered with the prodrug is not the prodrug or mitomycin C.

In on embodiment, instructions are provided to administer the chemotherapeutic agent concurrently or sequentially with administering the prodrug.

In another embodiment, the solid tumor is associated with breast cancer, colon cancer, colorectal cancer, stomach cancer, esophageal cancer, melanoma cancer, bladder cancer, or pancreatic cancer.

In yet another aspect, a product comprised of a vial containing a prodrug of mitomycin C in an amount that yields a therapeutically-effective amount of mitomycin C; and instructions to administer the contents within the vial in combination with a chemotherapeutic agent is provided.

In addition to the exemplary aspects and embodiments described above, further aspects and embodiments will become apparent by reference to the drawings and by study of the following descriptions.

Additional embodiments of the present methods will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims, particularly when considered in conjunction with the accompanying examples and drawings.

BRIEF DESCRIPTION OF THE DRAWINGS

FIG. 4B presents a detailed view of the results for selected study groups—Group 1 (control, untreated), Group 2 (liposome-entrapped doxorubicin), Group 3 (liposomal-mitomycin C prodrug) and Group 4 (liposomal-mitomycin C prodrug in combination with liposome-entrapped doxorubicin);

FIG. 5C, placebo liposomes (Group 1); FIG. 5D, liposomal-mitomycin C prodrug (Group 3); FIG. 5E, paclitaxel (Group 5); FIG. 5F, liposomal-mitomycin C prodrug in combination with paclitaxel (Group 6); FIG. 5G, liposome-entrapped doxorubicin (Group 2); FIG. 5H, liposomal-mitomycin C prodrug in combination with liposome-entrapped doxorubicin (Group 4);

DETAILED DESCRIPTION

I. Definitions

Figure 1:
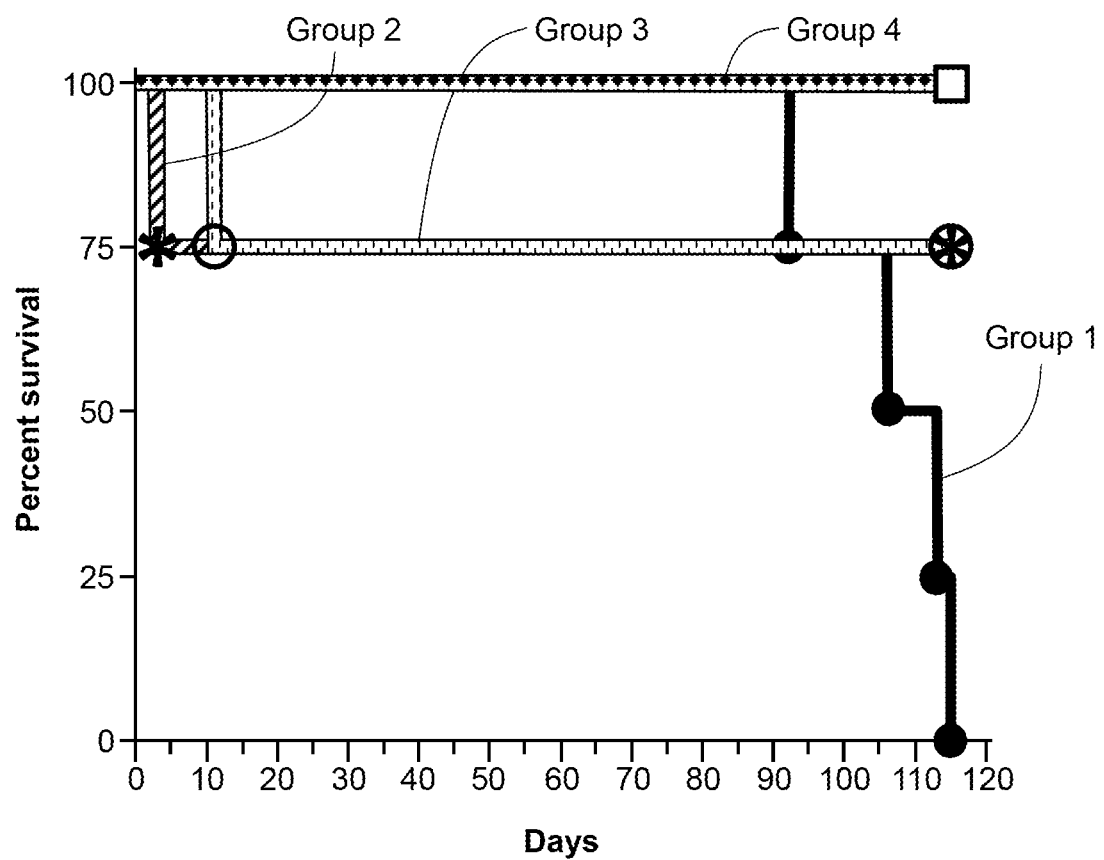
FIG. 1 is a graph showing percent survival of mice as a function of days in a study where the mice were treated with 45 mg/kg liposomal-mitomycin C prodrug (solid line, Group 1), or with 30 mg/kg liposomal-mitomycin C prodrug in combination with paclitaxel (line filled with diagonal stripes, Group 2), or with liposome-entrapped doxorubicin (line with dashed horizontal fill, Group 3), or with gemcitabine (line filled with solid diamonds, Group 4)

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

"Administering" or "administration" as used herein means the introduction of a foreign molecule into a cell or host. The term is intended to be synonymous with the term "delivery" or "delivering". Suitable routes of administration, without limitation, are intravenous, intra-arterial, intramuscular, subcutaneous, intraperitoneal, intrapleural, intrathecal, intravesical or intratumoral, intrasynovial, infusion, sublingual, transdermal, oral, or topical.

As used herein, the phrase "chemotherapeutic agent" is synonymous with and "antineoplastic agent" or "antiproliferative agent" and refers to compounds that prevent cancer, or hyperproliferative cells, from multiplying. Generally, antineoplastic agents may prevent cancer cells from multiplying by: (1) interfering with the cell's ability to replicate DNA and (2) inducing cell death and/or apoptosis in the cancer cells.

An amount of liposomal-mitomycin C prodrug that yields a therapeutically-effective amount of mitomycin C after administration is an amount of mitomycin C that is effective to ameliorate or minimize the clinical impairment or symptoms of the neoplasia, in either a single or multiple doses.

As used herein, a "neoplasm" or "neoplasia" means a proliferative disease characterized by the abnormal proliferation of cells. Typically, neoplasia is associated with cancer and tumor formation. As used herein a "solid tumor" is one that occurs in an organ, such as the breast or the colon.

The term "patient" refers to an individual afflicted with a disease characterized by neoplasia. In particular, a patient (i.e., a host) is an animal (i.e., mammal) or human.

As used herein, "pharmaceutical formulations" include formulations for human and veterinary use with no significant adverse effect. "Pharmaceutically acceptable carrier" as used herein refers to a composition or formulation that allows for the effective distribution of the agents of the instant invention in the physical location most suitable for their desired activity and "pharmaceutically acceptable carrier" refers to a buffer, stabilizer or other material well known to those skilled in the art. Such materials should be non-toxic and should not interfere with the efficacy of the active ingredient. The precise nature of the carrier or other material may depend on the route of administration.

As used herein, "prodrug" means a compound that is a drug precursor which, following administration to a subject, releases the drug in vivo via some chemical or physiological process such that the prodrug is converted into a product that is toxic to cells of a neoplasm.

As used herein "synergistic effect" or "therapeutic synergy" refers to a clinical observation wherein a combination of liposomal-mitomycin C prodrug and a chemotherapeutic agent that is not mitomycin C or liposomal-mitomycin C prodrug provides more than additive effect of each component used alone.

Reference to a "therapeutically effective amount," intends an amount of a compound sufficient to show benefit to the individual. This amount prevents, alleviates, abates, or otherwise reduces the severity of a symptom associated with neoplasia in a patient, such as a reduction in tumor mass or volume or a slowing of tumor growth rate.

The terms "treat," "treatment" and "therapeutic effect" as used herein refer to reducing or stopping a cell proliferation rate (e.g., slowing or halting tumor growth) or reducing the number of proliferating cancer cells.

Where a range of values is provided, it is intended that each intervening value between the upper and lower limit of that range and any other stated or intervening value in that stated range is encompassed within the disclosure. For example, if a range of 1 µm to 8 µm is stated, it is intended that 2 µm, 3 µm, 4 µm, 5 µm, 6 µm, and 7 µm are also explicitly disclosed, as well as the range of values greater than or equal to 1 µm and the range of values less than or equal to 8 µm.

The singular forms "a," "an," and "the" include plural referents unless the context clearly dictates otherwise. Thus, for example, reference to a "liposome" includes a single liposome as well as two or more of the same or different liposomes, reference to an "excipient" includes a single excipient as well as two or more of the same or different excipients, and the like.

II. Methods of Treatment

In one aspect, a method for treating a subject comprises providing a prodrug of mitomycin C in an amount that yields a therapeutically-effective amount of mitomycin C, and administering, or instructing to administer, in conjunction with administration of the prodrug, a chemotherapeutic agent. The prodrug of mitomycin C and the chemotherapeutic agents contemplated for co-administration therewith are described below.

A. Liposomal Mitomycin C Prodrug

The liposomal prodrug conjugate of mitomycin C provided for use in the methods described herein is, in one embodiment, comprised of mitomycin C releasably attached to a lipophilic or hydrophobic moiety, and generally is of the form:

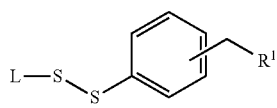

wherein L is a hydrophobic moiety, $R^1$ represents a mitomycin C residue covalently attached to the dithiobenzyl moiety. Orientation of the $CH_2R^1$ group is selected from the ortho position and the para position. Synthesis of the conjugate is described in U.S. Pat. Nos. 6,365,179; 6,984,396; and 7,303,760, each of which is incorporated by reference herein.

The hydrophobic moiety, L, is typically a lipid such as a diacylglycerol, a sterol, a phospholipid, derivatives of these lipids, other naturally-occurring lipids and their synthetic analogs. The hydrophobic moiety is suitable for incorporation into a liposomal bilayer, to anchor the mitomycin C conjugate to a liposomal delivery vehicle.

The liposomal-mitomycin C prodrug conjugate upon exposure to reducing conditions, i.e., a reducing agent such as cysteine or glutathione, decomposes to yield mitomycin C. That is, thiolytic cleavage of the conjugate yields mitomycin C and non-toxic by products of the hydrophobic moiety and the dithiobenzyl moiety. As can be appreciated, the prodrug conjugate can be readily incorporated into liposomes for administration in vivo to a subject. The prodrug conjugate is not toxic, and after administration and upon exposure to endogenous reducing agents or exposure to an exogenous reducing agent, the conjugate decomposes to yield mitomycin C in its native state and with biological activity.

Studies conducted in support of the methods described herein used the prodrug conjugate para-diacyldiglyceroldithiobenzal-mitomycin C. The conjugate was synthesized as set forth in Example 1 and was incorporated into a liposomal delivery vehicle, also as described in Example 1.

B. Chemotherapeutic Agents

The method comprises administration to a patient in need, such as a patient with cancerous cells, a liposomal mitomycin C prodrug in combination with a (second) chemotherapeutic agent. The second chemotherapeutic agent is not a liposomal mitomycin C prodrug or mitomycin C or a non-liposomal mitomycin C prodrug. The chemotherapeutic agents contemplated for use in conjunction with the liposomal mitomycin C prodrug are not limited to any particular compounds or class of compounds. Based on the studies discussed herein below it has been discovered that liposomal-mitomycin C prodrug administered in combination with certain chemotherapeutic agents yields a synergistic effect.

In one embodiment, the chemotherapeutic agent administered in combination with liposomal-mitomycin C prodrug is gemcitabine. Gemcitabine is the generic name assigned to 2'-deoxy-2',2'-difluoro-cytidine. It is commercially available as the monohydrochloride salt, and as the .beta.-isomer. It is also known chemically as 1-(4-amino-2-oxo-1H-pyrimidin-1-yl)-2-desoxy-2,2-difluororibose. Gemcitabine is disclosed in U.S. Pat. Nos. 4,808,614 and 5,464,826, which are incorporated herein by reference for their teaching of how to synthesize, formulate, and use gemcitabine for treating susceptible neoplasms. The commercial formulation of gemcitabine hydrochloride is indicated as first-line treatment for patients with locally advanced (nonresectable Stage II or Stage III) or metastatic (Stage IV) adenocarcinoma of the pancreas, and, in combination with cisplatin or carboplatin, in patients with Non-small cell lung cancer and bladder cancer.

In another embodiment, the chemotherapeutic agent administered in combination with liposomal-mitomycin C prodrug is a vinca alkaloid, such as vinblastine, vinorelbine, vincristine, or vindesine.

In another embodiment, the chemotherapeutic agent administered in combination with liposomal-mitomycin C prodrug is an anthracycline antibiotic, such as doxorubicin or daunorubicin. These anthracycline drugs are widely used in human cancer chemotherapy. And cause DNA damage such as fragmentation and single-strand breaks. The mechanism of action of anthracyclines involves the inhibition of RNA and DNA syntheses. In one embodiment, the doxorubicin or daunorubicin are provided in liposome-entrapped form. pegylated Liposome-entrapped doxorubicin is known by the trade names of DOXIL®, CAELYX®, and LIPO-DOX®, and liposome-entrapped daunorubicin is known by the trade name DAUNOXOME®.

In another embodiment, the chemotherapeutic agent administered in combination with liposomal-mitomycin C prodrug is a taxane. Taxanes are diterpenes produced by the plants of the genus *Taxus* (yews), and are widely used as chemotherapy agents. Taxane agents include paclitaxel (TAXOL®) and docetaxel (TAXOTERE®).

In another embodiment, the chemotherapeutic agent administered in combination with liposomal mitomycin C prodrug is a fluoropyrimidine. Fluoropyrimidines are antimetabolite drugs widely used in the treatment of cancer including colorectal and breast cancer and cancers of the aerodigestive tract. The fluoropyrimidines include the drugs 5-fluorouracil (5-FU) and prodrugs of 5-FU, such as capecitabine and tegafur. In one embodiment, the fluoropyrimidine chemotherapeutic agent administered in combination with liposomal mitomycin C prodrug is a prodrug for 5-FU, such as capecitabine. Capecitabine is a fluoropyrimidine carbamate with antineoplastic activity. It is an orally administered systemic prodrug of 5'-deoxy-5-fluorouridine (5'-DFUR) which is converted to 5-fluorouracil. The chemical name for capecitabine is 5'-deoxy-5-fluoro-N-[(pentyloxy)carbonyl]-cytidine. It is marketed in the United States as XELODA® (Roche Laboratories). It is indicated for the treatment of patients with metastatic breast cancer and colorectal tumors by oral route. Capecitabine is described in U.S. Pat. No. 5,472,949.

Methods for the safe and effective administration of these chemotherapeutic agents are known to those skilled in the art. In addition, their administration is described in the standard literature. For example, the administration of many of the chemotherapeutic agents is described in the "Physicians' Desk Reference" (PDR), e.g., 1996 edition (Medical Economics Company, Montvale, N.J.).

C. Exemplary Studies in Support of the Method of Treatment

In a first study, prodrug conjugate of mitomycin C was prepared and incorporated into a liposome delivery platform as described in Example 1. The prodrug conjugate incorporated into a liposome delivery platform is referred to as "liposomal-mitomycin C prodrug." The liposomal-mitomycin C prodrug conjugate was administered alone or in combination with paclitaxel, liposome-entrapped doxorubicin, and gemcitabine to mice. As described in Example 2, four groups of mice were treated with intravenous injection of the liposomal-mitomycin C prodrug (Group 1), or with liposomal-mitomycin C prodrug in combination with liposome-entrapped doxorubicin (Group 2), or with liposomal-mitomycin C prodrug in combination with paclitaxel (Group 3) or with liposomal-mitomycin C prodrug in combination with gemcitabine (Group 4). The mice were observed for 100 days, and the percent survival is reported in FIG. 1. Treatment with liposomal-mitomycin C prodrug in combination with paclitaxel (Group 3, line with dashed horizontal fill) resulted in an acute 20% toxic death rate and treatment with liposomal-mitomycin C prodrug at the 45 mg/kg dose resulted in a 20% toxic death observed at about day 90 of the study. The animals treated with a combined treatment of liposomal-mitomycin C prodrug and gemcitabine (Group 4, solid line in FIG. 1) had no toxic deaths.

Figure 2:
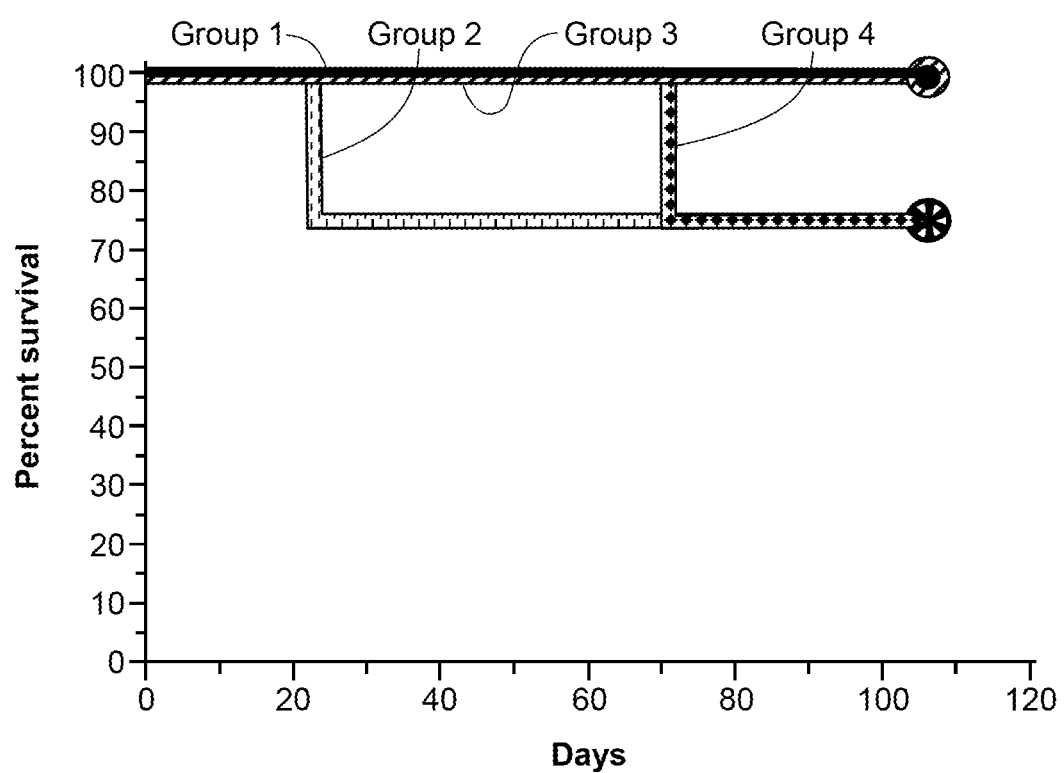
FIG. 2 is a graph showing percent survival of mice as a function of days in a study where the mice were treated with 30 mg/kg liposomal-mitomycin C prodrug (line with solid fill; Group 1) or with 20 mg/kg liposomal-mitomycin C prodrug in combination with liposome-entrapped doxorubicin (Group 2; line with diagonal stripes fill), with paclitaxel (Group 3, line with dashed horizontal fill), or with gemcitabine (Group 4, line filled with solid diamonds)

Another study similar to that outline in Example 2 was conducted. In this study, the dose of liposomal-mitomycin C prodrug was 30 mg/kg when administered as a single agent or 20 mg/kg when administered in combination with paclitaxel, liposome-entrapped doxorubicin, or gemcitabine. After treatment, as detailed in Example 3, the mice were observed for 100 days, and the results are shown in FIG. 2. Treatment with liposomal-mitomycin C prodrug at a dose of 30 mg/kg resulted in no toxic deaths (line with solid fill; Group 1). Liposomal-mitomycin C prodrug at a dose of 30 mg/kg in combination with paclitaxel (Group 3, line with diagonal stripes fill), with liposome-entrapped doxorubicin (Group 2; line with dashed horizontal fill), or with gemcitabine (Group 4, line filled with solid diamonds) each resulted in 20% toxic deaths.

The sequence of dosing the chemotherapeutic agents was explored in a study described in Example 3. Mice were treated via intravenous (iv) injection with liposome-entrapped doxorubicin and after 48 hours with liposomal-mitomycin C prodrug. Another group of mice was treated first with liposomal-mitomycin C prodrug and after 48 hours with liposome-entrapped doxorubicin. Over the observation period following treatment with the chemotherapeutic agents, there was reduction of the weight in both groups. One mouse died at the group that was treated first with liposomal-mitomycin C prodrug. According to the weight results there was no substantial difference in toxicity between the two different treatments.

The clearance of mitomycin C from the blood after administration in vivo in the form of a prodrug was determined in a study described in Example 5. A prodrug of mitomycin C was prepared and incorporated into a liposome delivery platform. The prodrug was administered to mice, alone or in combination with liposome-entrapped doxorubicin. Another group of mice were treated with liposome-entrapped doxorubicin alone. Blood was drawn 1 hour and 48 hours after dosing, and the concentrations of mitomycin C and/or doxorubicin in plasma were measured.

Figure 3A:
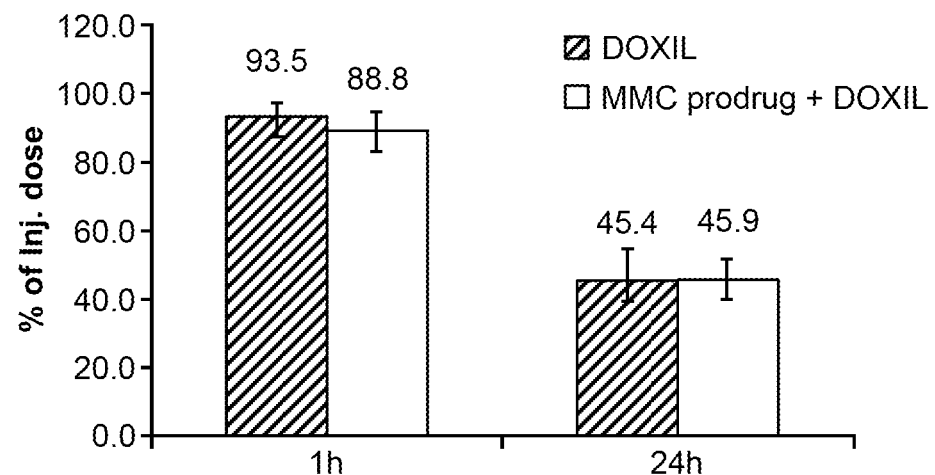
FIG. 3A is a bar graph showing the percent of injected dose of doxorubicin in plasma, at 1 hour and 24 hours post treatment in vivo with liposome-entrapped doxorubicin alone (filled bars) or with the combination treatment of liposomal-mitomycin C prodrug and liposome-entrapped doxorubicin (open bars).
Figure 3B:
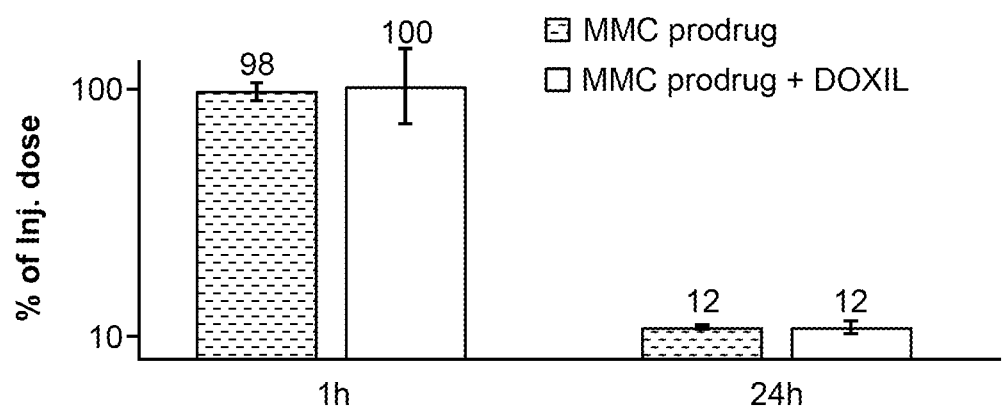
FIG. 3B is a bar graph showing the percent of injected dose of liposomal mitomycin C prodrug in plasma, at 1 hour and 24 hours post administration in vivo of liposomal-mitomycin C prodrug alone (filled bars) or a combination treatment of liposomal-mitomycin C prodrug and liposome-entrapped doxorubicin (open bars)

FIG. 3A shows the percent of injected dose of doxorubicin in plasma at the 1 hour and 24 hour sampling times for mice treated with liposome-entrapped doxorubicin alone (filled bars) or with the combination treatment of liposomal-mitomycin C prodrug and liposome-entrapped doxorubicin (open bars). FIG. 3B shows the percent of mitomycin C in plasma at the 1 hour and 24 hour sampling times for mice treated with liposomal-mitomycin C prodrug alone (filled bars) or with the combination treatment of liposomal-mitomycin C prodrug and liposome-entrapped doxorubicin (open bars). The rate of liposome-entrapped doxorubicin clearance is slower than that of liposomal-mitomycin C prodrug and there was no change in the clearance when both the prodrug and liposome-entrapped doxorubicin were co-injected.

Therapeutic efficacy of the liposomal-mitomycin C prodrug was evaluated in a series of studies described in Examples 6-11. In the study described in Example 6, tumor-bearing mice were treated with a single agent therapy (liposomal-mitomycin C prodrug, liposome-entrapped doxorubicin, gemcitabine and paclitaxel) or with a combination therapy of liposomal-mitomycin C prodrug in combination with liposome-entrapped doxorubicin, gemcitabine or paclitaxel. Survival of the animals was measured for 45 days post-tumor inoculation and the results in shown in FIGS. 4A-4B.

Figure 4A:
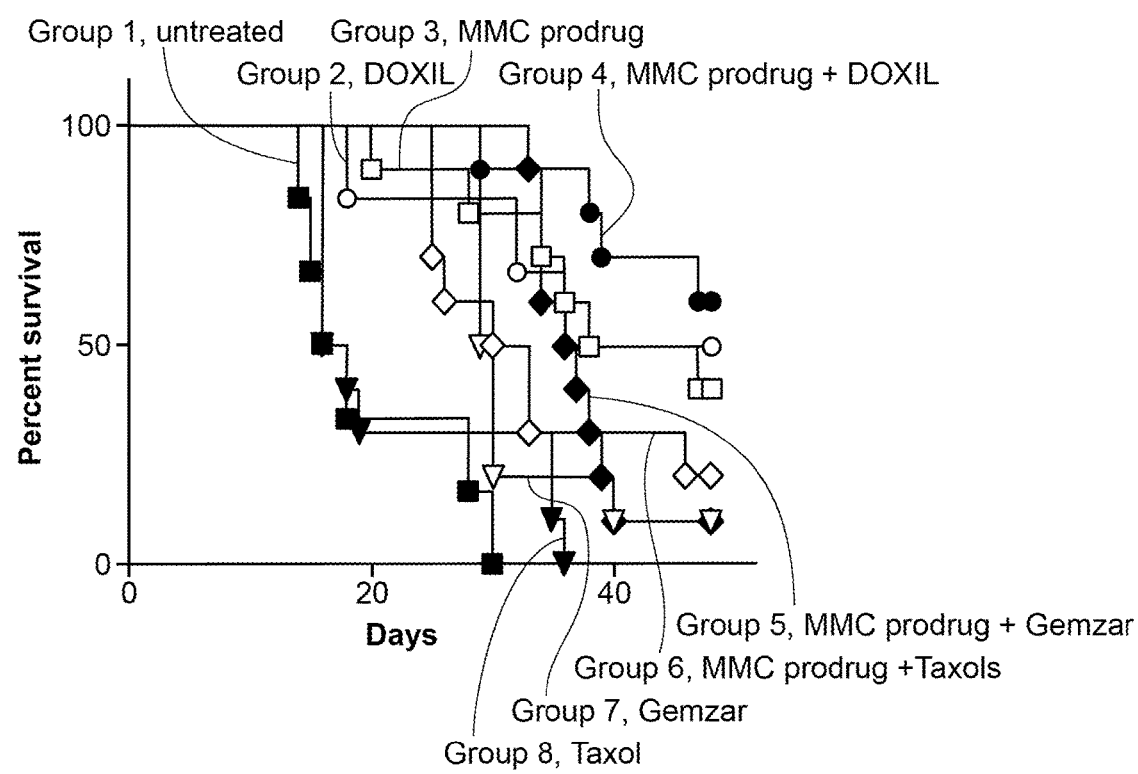
FIGS. 4A-4B show the percent survival as a function of days post tumor-inoculation for mice inoculated with C26 tumor cells and left untreated (Group 1, solid squares) or treated with one of the following: liposome-entrapped doxorubicin (Group 2, open circles); liposomal-mitomycin C prodrug (Group 3, open squares); liposomal-mitomycin C prodrug in combination with liposome-entrapped doxorubicin (Group 4, solid circles); liposomal-mitomycin C prodrug and gemcitabine (Group 5, solid diamonds); liposomal-mitomycin C prodrug in combination with paclitaxel (Group 6, open diamonds); gemcitabine (Group 7, open triangles); or paclitaxel (Group 8, inverted triangles).
Figure 4B:
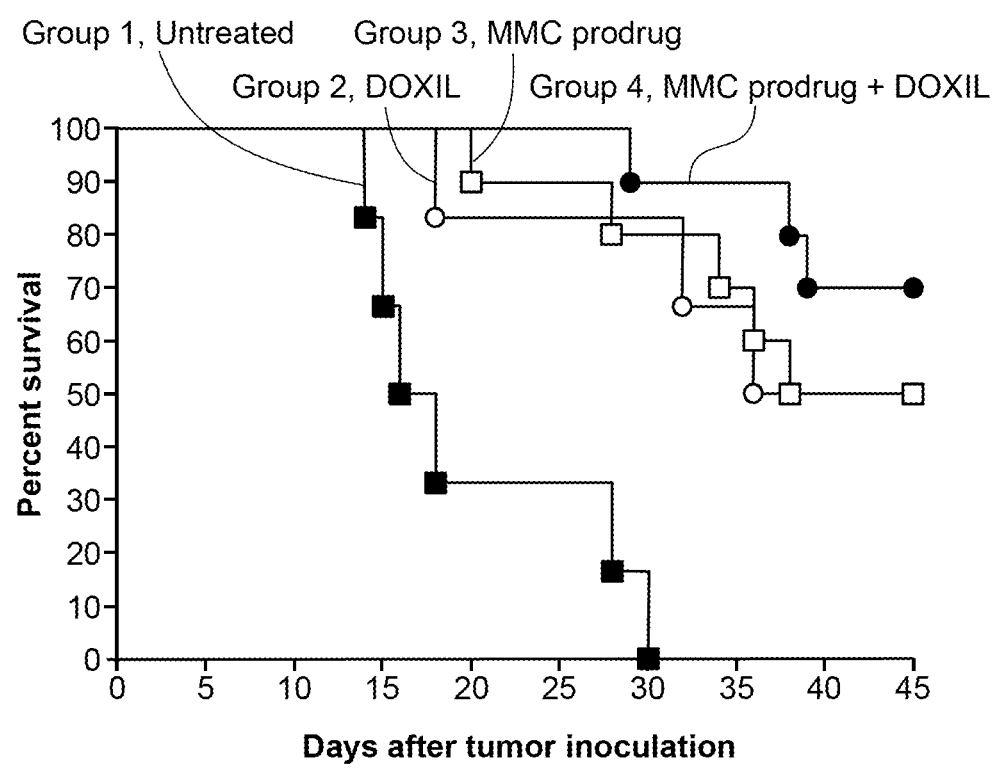

Survival results for all eight study groups are shown in FIG. 4A. FIG. 4B presents a detail view of the results for selected study groups—Group 1 (control, untreated), Group 2 (liposome-entrapped doxorubicin), Group 3 (liposomal-mitomycin C prodrug) and Group 4 (liposomal-mitomycin C prodrug in combination with liposome-entrapped doxorubicin). All tumor-bearing animals left untreated (Group 1, solid squares, FIGS. 4A-4B) died by day 30 of the study, with a median day of survival of 17 days. Half (50% survival) of the animals treated with liposome-entrapped doxorubicin (Group 2, open circles) survived for the 45 day observation period, with a median day of survival of 40.5 days. Animals treated with liposomal-mitomycin C prodrug (Group 3, open squares) fared better than those treated with liposome-entrapped doxorubicin, with a median day of survival of 41.5 days. A combination therapy of liposomal-mitomycin C prodrug in combination with liposome-entrapped doxorubicin (Group 4, solid circles) had the best survival rate of any of the test groups, with 70% of the animals surviving the 45 day observation period, and a median day of survival of greater than 45 days. Single agent treatment with paclitaxel (Group 8, inverted triangles) or with gemcitabine (Group 7, open triangles) fared poorly, with nearly all animals failing to survive the study period. Combination of liposomal-mitomycin C prodrug and gemcitabine (Group 5, solid diamonds) or paclitaxel (Group 6, open diamonds) had longer survival rates relative to treatment with the single agents (gemcitabine, paclitaxel). The data illustrates that liposomal-mitomycin C prodrug in combination with a second chemotherapeutic agent results in improved survival rates of tumor-bearing animals relative to treatment with the second chemotherapeutic agent alone.

In another described in Example 7, mice with the N87 human gastric tumor model were treated with a single agent therapy (liposomal-mitomycin C prodrug, liposome-entrapped doxorubicin, or paclitaxel) or with a combination therapy of liposomal-mitomycin C prodrug in combination with liposome-entrapped doxorubicin or with paclitaxel. Survival of the animals was measured for 50 days post-tumor inoculation and the results in shown in FIGS. 5A-5B. Tumor size in the animals was measured for 48 days post tumor inoculation, and the results are shown in FIGS. 5C-5H.

Figure 5A:
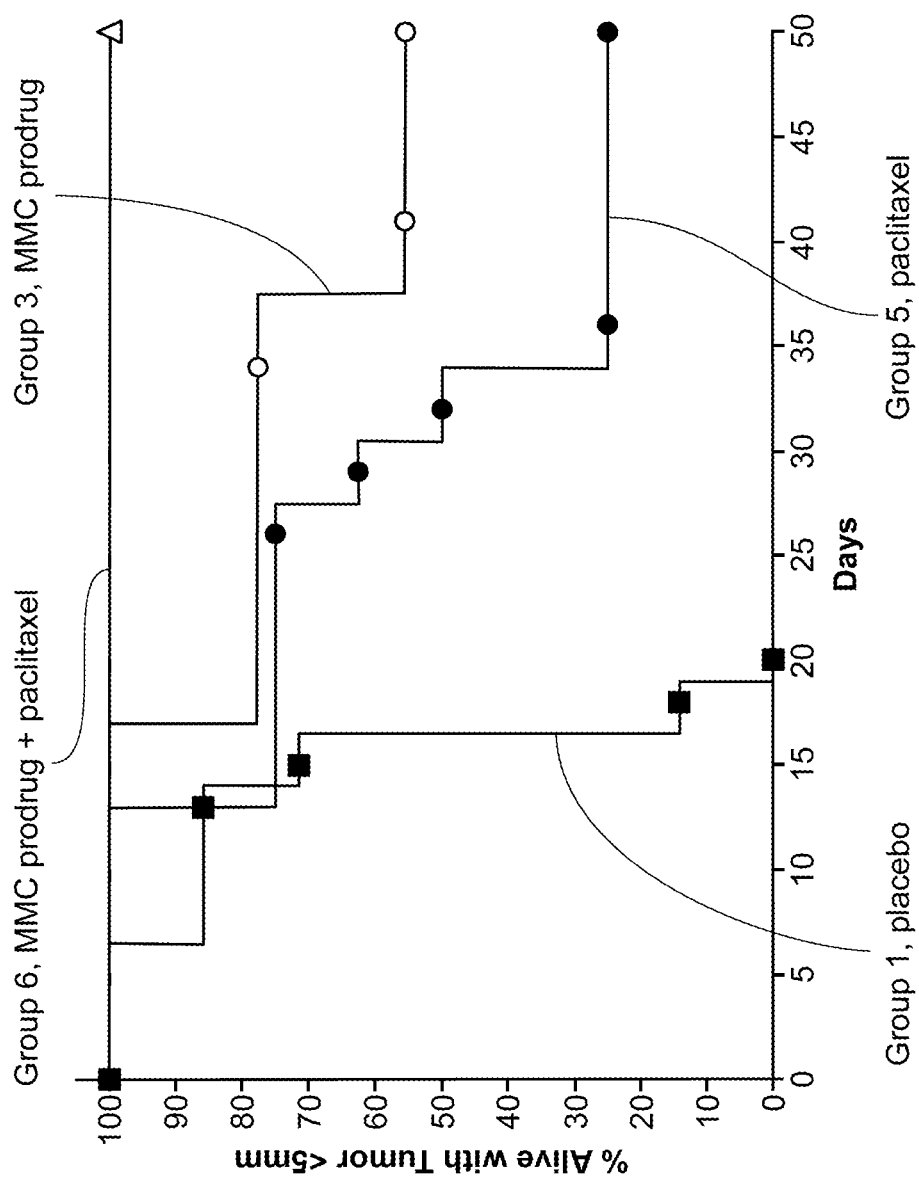
FIGS. 5A-5B are graphs of percent of animals surviving with a tumor volume less than 5 mm as a function of days post tumor inoculation, for mice bearing a human gastric tumor model and treated with placebo liposomes (Group 1, solid squares, FIGS. 5A-5B); paclitaxel (Group 5, solid circles, FIG. 5A); liposomal mitomycin C prodrug (Group 3, open circles, FIGS. 5A-5B); liposomal-mitomycin C prodrug in combination with paclitaxel (Group 6, open triangles, FIG. 5A); liposomal-mitomycin C prodrug in combination with liposome-entrapped doxorubicin (Group 4, open squares, FIG. 5B); or liposome-entrapped doxorubicin (Group 2, open triangles, FIG. 5B)

FIG. 5A shows the percent of surviving animals with tumor volumes less than 5 mm when treated with placebo liposomes (Group 1, solid squares) or with paclitaxel (Group 5, solid circles), liposomal-mitomycin C prodrug (Group 3, open circles) or liposomal-mitomycin C prodrug in combination with paclitaxel (Group 6, open triangles). The survival results show that the combination of liposomal-mitomycin C prodrug and paclitaxel (Group 6, open triangles) is statistically significantly more effective than liposomal-mitomycin C prodrug alone (Group 3, open circles) and is also statistically significantly more effective than paclitaxel alone (Group 5, solid circles). As seen, all nine animals in the group treated with the combination therapy survived for 50 days, and all nine animals were tumor free. In contrast, four of the nine animals treated with liposomal-mitomycin C prodrug alone were tumor free at observation day 50, and two of eight animals treated with paclitaxel alone were tumor free on observation day 50. All seven animals treated with placebo liposomes (Group 1, solid squares) developed tumors and all seven died by day 20 of the study.

Figure 5B:
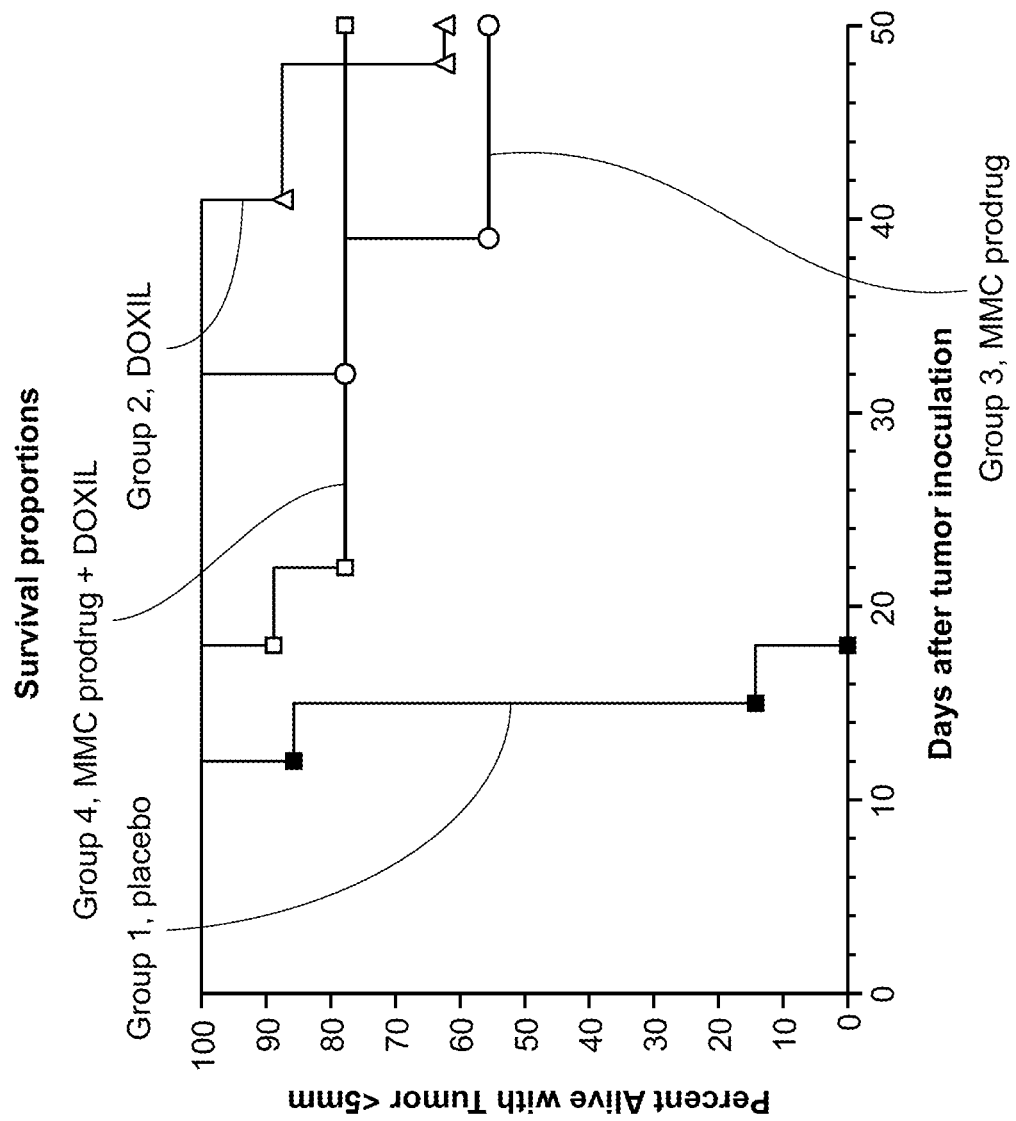

FIG. 5B shows the results for animals treated with liposomal-mitomycin C prodrug in combination with liposome-entrapped doxorubicin (Group 4, open squares) and with liposome-entrapped doxorubicin alone (Group 2, open triangles). Results for animals treated with liposomal-mitomycin C prodrug alone (Group 3, open circles) and with placebo liposomes (Group 1, solid squares) are also shown in FIG. 5B, for ease of reference. The combination of liposomal-mitomycin C prodrug with liposome-entrapped doxorubicin was more effective in inhibiting tumor growth than liposomal-mitomycin C prodrug alone and was more effective in inhibiting tumor growth than liposome-entrapped doxorubicin alone. Liposomal-mitomycin C prodrug in combination with liposome-entrapped doxorubicin resulted in two toxic deaths (days 18-20) however all other (7) mice were cured and were tumor free at the end of the observation period, similar to the observation made for the animals treated with liposomal-mitomycin C prodrug in combination with paclitaxel (FIG. 5A, Group 6). Animals treated with liposome-entrapped doxorubicin or with liposomal-mitomycin C prodrug alone (as single agents) resulted in 3/8 animals and 3/9 animals, respectively, failing to achieve tumor resolution. The data in FIG. 5B show that combination of liposomal-mitomycin C prodrug in combination with liposome-entrapped doxorubicin is more effective in inhibiting tumor growth than either of the agents administered alone as a single agent.

Figures 5C, 5D:
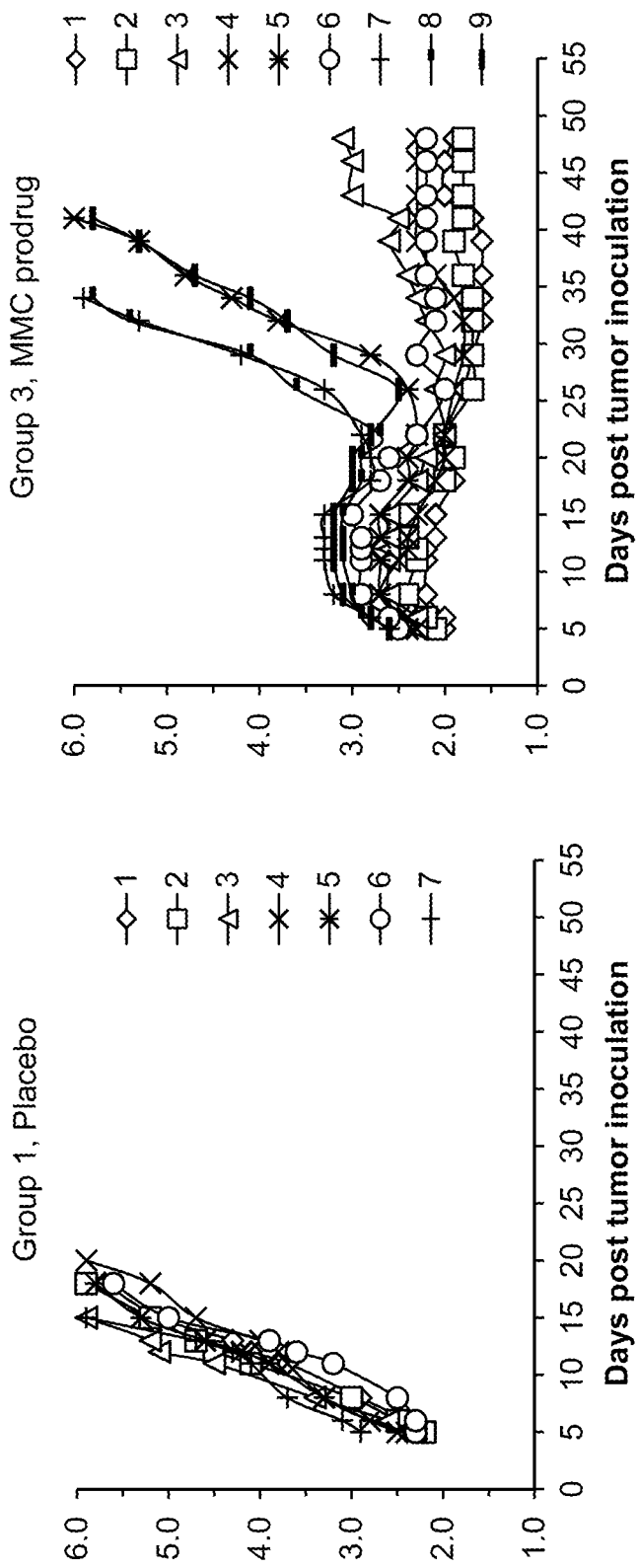
FIGS. 5C-5H are graphs showing the tumor volume, in mm, of each animal in Groups 1-6 detailed for FIGS. 5A-5B as a function of days post tumor inoculation, for the animals in test.
Figures 5E, 5F:
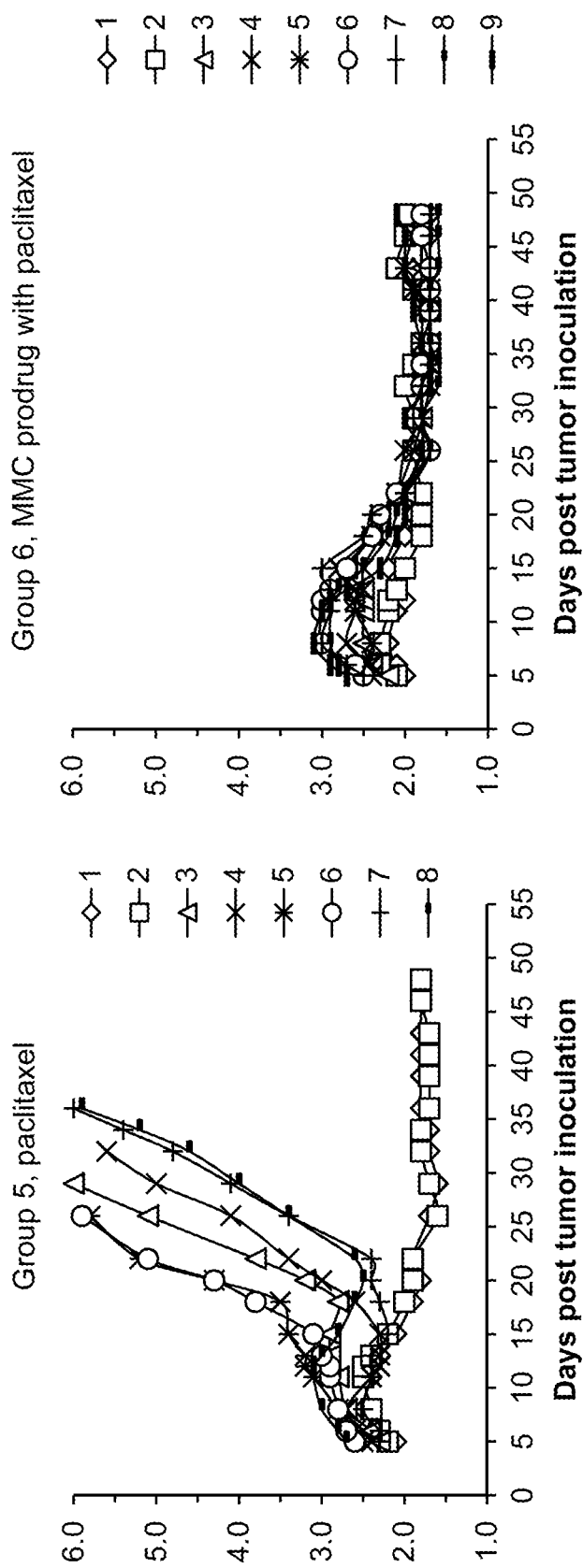
Figures 5G, 5H:
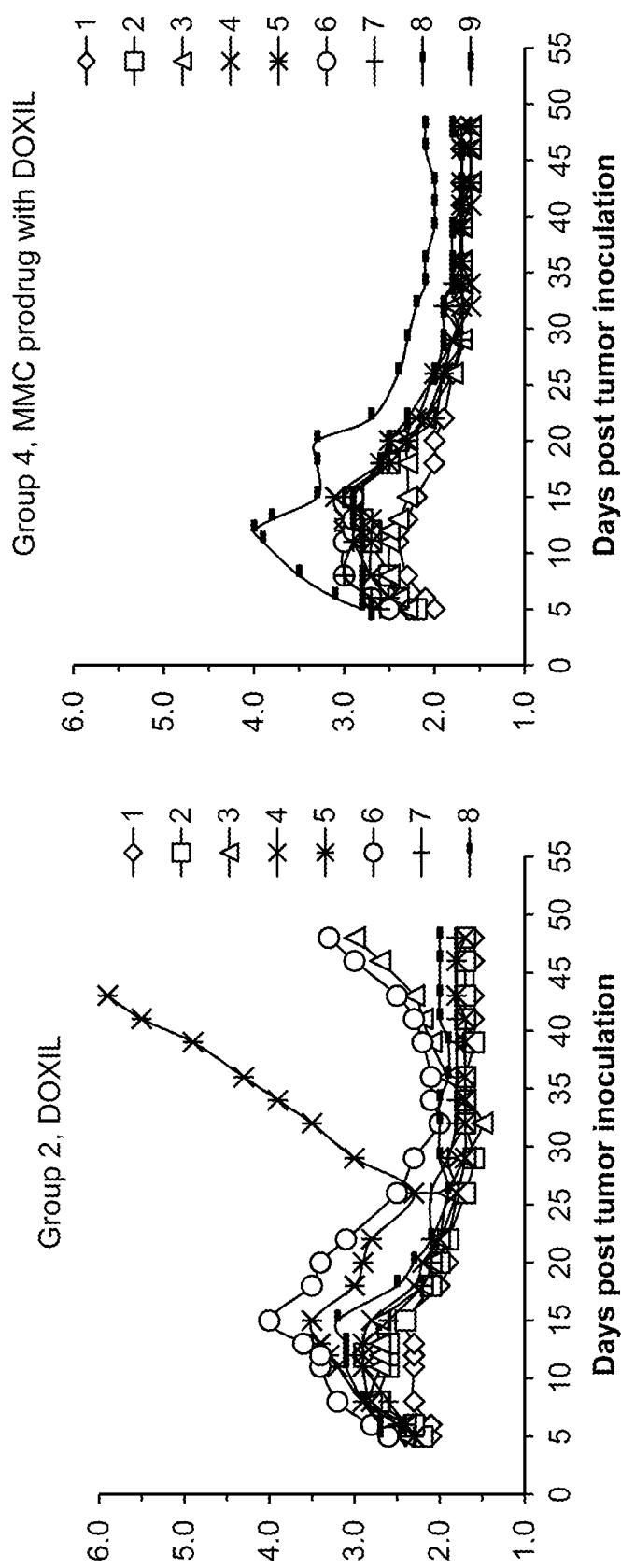

The tumor volume of the animals in each of the test Groups 1-6 was measured on each day of the study, and the results are presented in FIGS. 5C-5H. Treatment with a combination of liposomal-mitomycin C prodrug and a second chemotherapeutic agent, such as liposome-entrapped doxorubicin (FIG. 5H) and paclitaxel (FIG. 5F) achieved a remarkable reduction in tumor volume. Reduction in tumor volume was not observed in the animals treated with the chemotherapeutic agents administered as single agents (FIG. 5G, liposome-entrapped doxorubicin alone; FIG. 5E, paclitaxel alone; FIG. 5D, liposomal mitomycin C prodrug alone); that is, only the combination therapy of liposomal-mitomycin C prodrug in combination with a second agent provided the reduction in tumor volume.

Figure 6:
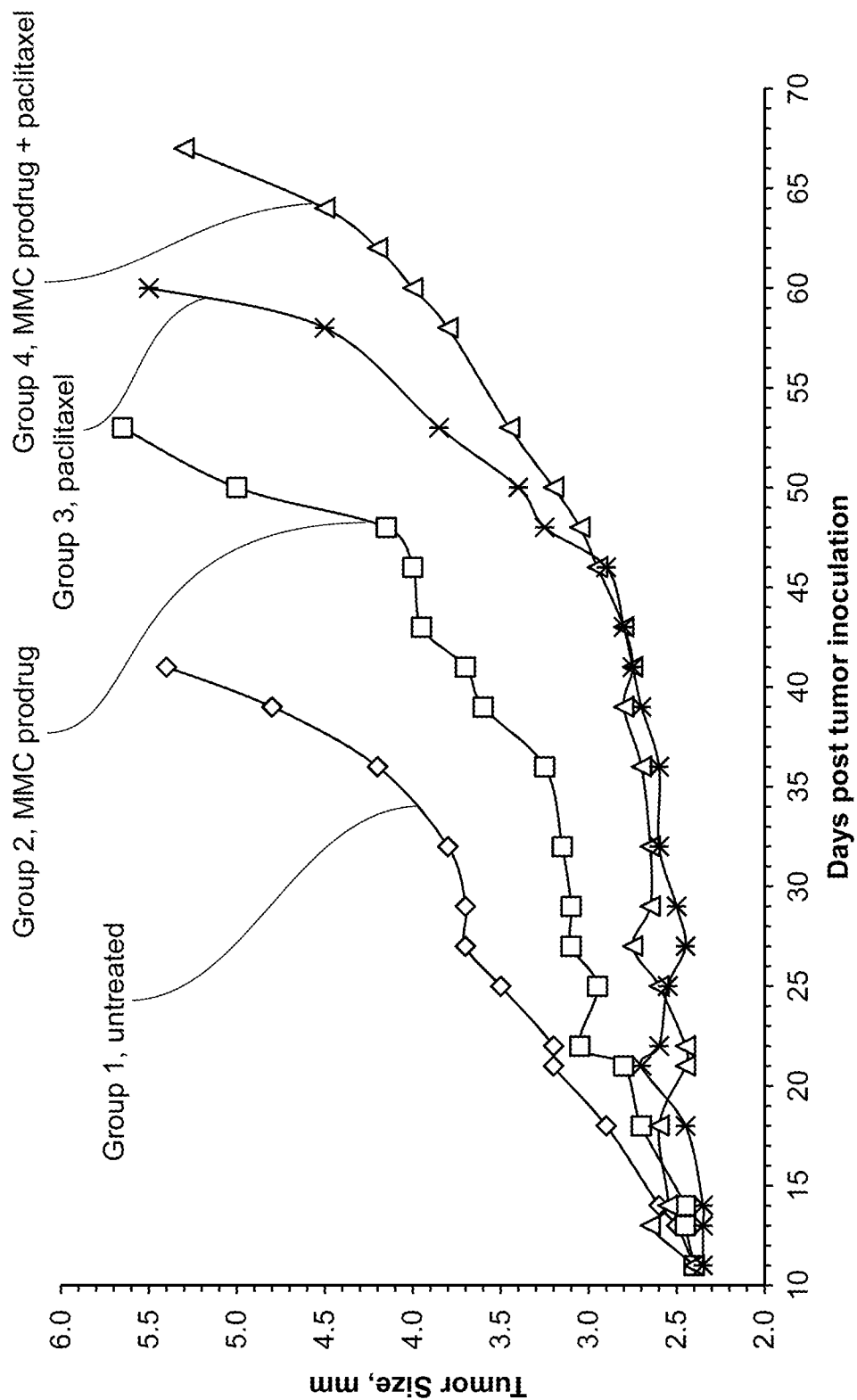
FIG. 6 is a graph of tumor size, in mm, as a function of days post inoculation in mice with a human A375 melanoma subcutaneous tumor, for animals untreated (Group 1, triangles) or treated with liposomal-mitomycin C prodrug (Group 2, squares), paclitaxel (Group 3, X symbols) or a combination of liposomal-mitomycin C prodrug and paclitaxel (Group 4, triangles)

Another study was conducted using a human A375 melanoma subcutaneous tumor model. As described in Example 8, after tumor inoculation, mice were treated with liposomal mitomycin C prodrug (Group 2), with paclitaxel (Group 3) or with a combination of liposomal mitomycin C prodrug and paclitaxel (Group 4). Another group of animals was untreated, as a control (Group 1). The tumor size of the animals in each treatment group was measured, and the median tumor size (in mm) is shown in FIG. 6 as a function of days post tumor inoculation. Left untreated (Group 1, diamonds), the tumor exceeds 5 mm in size about 40 days after inoculation. Tumor-bearing animals treated with a combination of liposomal mitomycin C prodrug and paclitaxel (Group 4, triangles) had a plateau period of about 30 days with relatively little increase in tumor size. In the animals treated with a combination that comprised liposomal mitomycin C prodrug, tumor size exceeded 5 mm about 65 days post inoculation. Animals treated with a single agent therapy, liposomal mitomycin C prodrug (Group 2, squares) or paclitaxel (Group 3, X symbols), had either a shorter plateau period of attenuated tumor growth or an increase in tumor growth sooner than animals treated with the combination therapy. The data from this study shows that the combination of liposomal mitomycin C prodrug and paclitaxel was more effective in tumor growth inhibition than liposomal mitomycin C prodrug alone and was more effective in tumor growth inhibition than paclitaxel alone.

A study was designed to compare efficacy of liposomal mitomycin C prodrug to mitomycin C as a free agent. In this study, described in Example 9, mice with a 4T1 breast mouse tumor were randomized into treatment groups for treatment with one of the following agents on day five post tumor inoculation: mitomycin C (Group 2), liposome-entrapped doxorubicin (Group 3), mitomycin C prodrug (Group 4), mitomycin C and liposome-entrapped doxorubicin (Group 5) or mitomycin C prodrug in combination with liposome-entrapped doxorubicin (Group 6). One group of animals was left untreated as a control (Group 1). Tumor size was measured as a function of days post inoculation, and the results are shown in FIG. 7.

Figure 7:
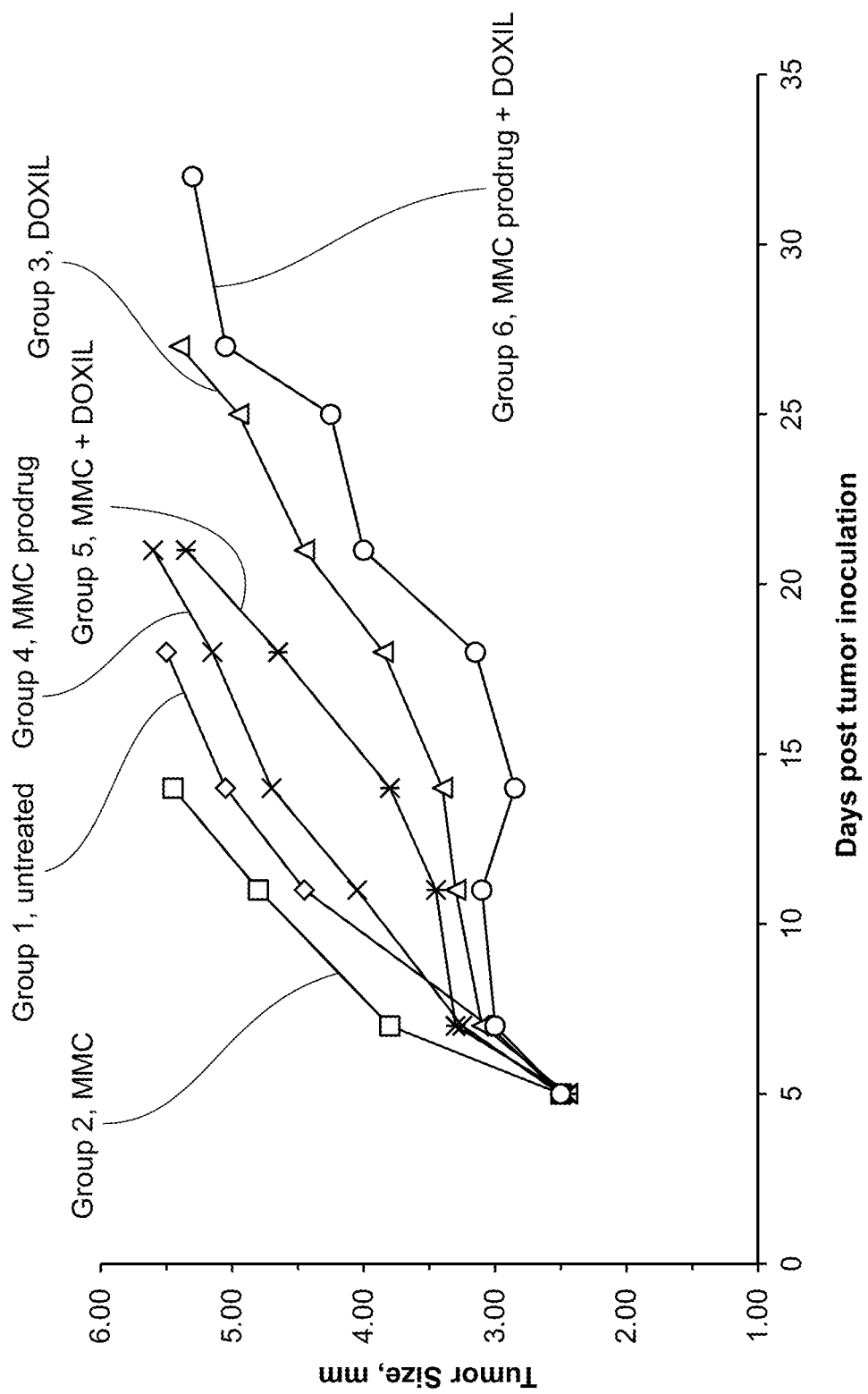
FIG. 7 is a graph showing median tumor size, in mm, as a function of days post inoculation in mice with a subcutaneous 4T1 breast mouse tumor, for animals untreated (Group 1, triangles) or treated with mitomycin C (Group 2, squares) as a free agent, liposome-entrapped doxorubicin (Group 3, triangles), liposomal-mitomycin C prodrug (Group 4, X symbols), mitomycin C and liposome-entrapped doxorubicin (Group 5, * symbols) or liposomal-mitomycin C prodrug in combination with liposome-entrapped doxorubicin (Group 6, circles)

With reference to FIG. 7, animals treated with mitomycin C as a free agent (Group 2, squares) or left untreated (Group 1, triangles) showed a continued growth in tumor size, as did animals treated with mitomycin C prodrug (Group 4, X symbols). A combination treatment of mitomycin C prodrug and liposome-entrapped doxorubicin (Group 6, circles) was effective to provide a period of about 2 weeks with little or no tumor growth, followed by a growth phase at a rate slower than that observed for animals treated with single agent therapies (mitomycin C as a free agent (Group 2, squares); liposome-entrapped doxorubicin (Group 3, triangles); mitomycin C prodrug (Group 4, X symbols)) and at a rate slower than that observed for animal treated with a combination of mitomycin C free agent (not a prodrug) and liposome-entrapped doxorubicin (Group 5, * symbols).

Using an N87 human gastric tumor model in mice, efficacy of free mitomycin C alone and in combination with a second agent was compared to efficacy in tumor inhibition of liposomal-mitomycin C prodrug alone and in combination with a second agent. As described in Example 10, mice bearing an N87 gastric tumor were separated into groups for treatment with mitomycin C (Group 2), mitomycin C prodrug (Group 3), paclitaxel (Group 4), mitomycin C and paclitaxel (Group 5) or mitomycin C prodrug and paclitaxel (Group 6). One group of animals was left untreated as a control (Group 1). Tumor size was measured as a function of days post inoculation was measured for animals in each treatment group.

Figure 8:
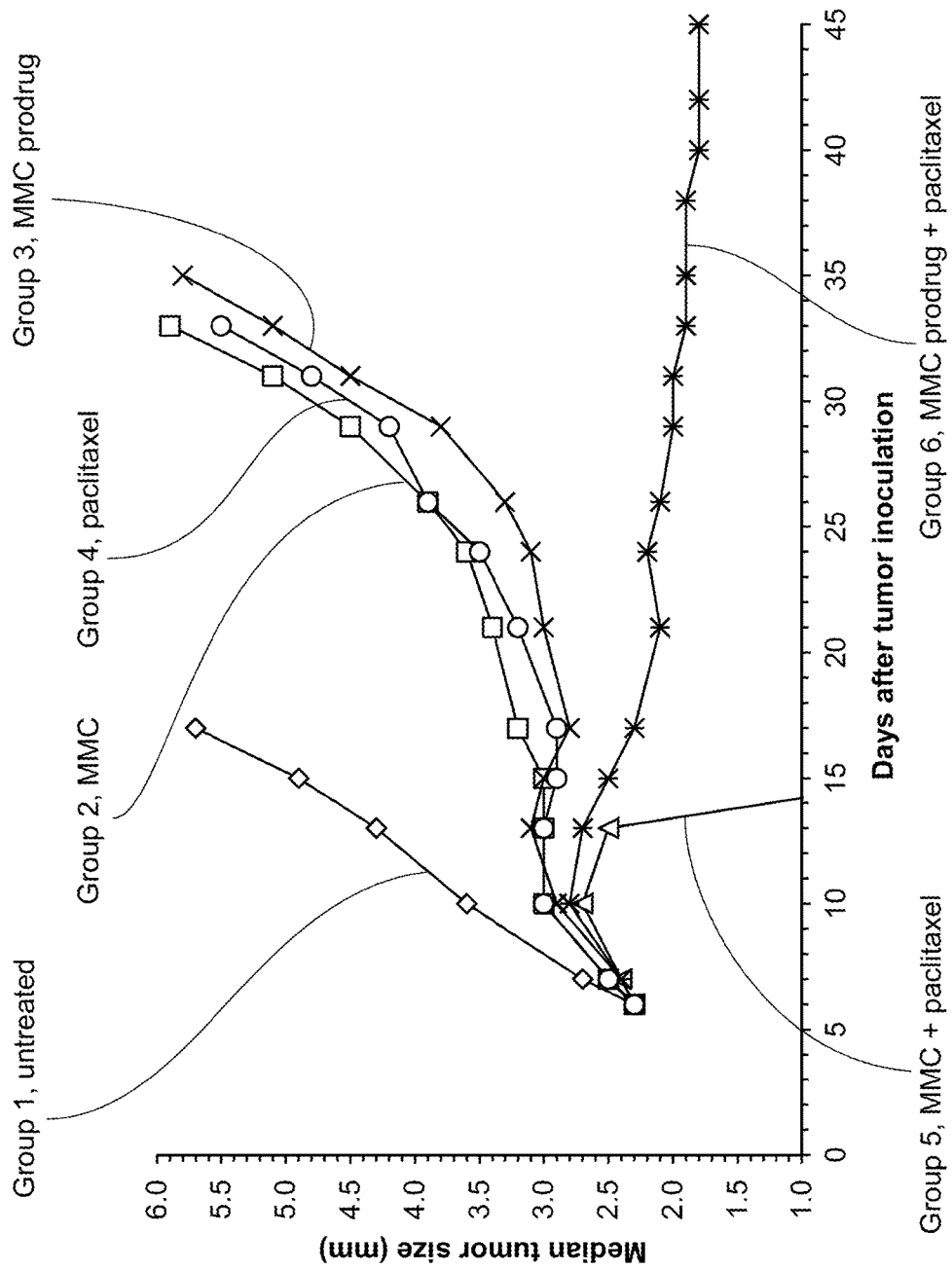
FIG. 8 is a graph showing median tumor size, in mm, as a function of days post inoculation in mice with a human gastric tumor, for animals untreated (Group 1, triangles) or treated with mitomycin C as a free agent, not a prodrug, (Group 2, squares), liposomal-mitomycin C prodrug (Group 3, X symbols), paclitaxel (Group 4, circles), free mitomycin C and paclitaxel (Group 5, triangles) or a combination of liposomal-mitomycin C prodrug and paclitaxel (Group 6, * symbols).

The results obtained showed that the combination of liposomal-mitomycin C prodrug and paclitaxel was more effective in inhibiting tumor growth than liposomal-mitomycin C prodrug alone and was more effective in inhibiting tumor growth than paclitaxel alone. Although initial observations suggested the combination therapy of liposomal-mitomycin C prodrug and paclitaxel was not superior to the combination of free mitomycin C and paclitaxel, inspection of the data showed that treatment with free mitomycin C and paclitaxel in combination was toxic to the animals, as evidenced by two deaths in the treatment group and weight loss of greater than 20%. Evaluation of the data after removing those mice with unacceptable toxicity (toxic deaths and drop >20% of weight) is presented in FIG. 8. The data in FIG. 8 show the severe toxicity of the combined treatment of free mitomycin C and paclitaxel (Group 5, triangles). The data also shows the continuous increase in tumor size in animals treated with mitomycin C (Group 2, squares), liposomal-mitomycin C prodrug (Group 3, X symbols), paclitaxel (Group 4, circles). The data also show that of the treatment regimens, the combination of liposomal-mitomycin C prodrug and paclitaxel (Group 6, * symbols) was non-toxic and provided a reduction in tumor size. Of the treatment regimens, combination therapy with liposomal-mitomycin C prodrug and paclitaxel was the only effective treatment in the study.

D. Treatment Modalities and Patient Populations

As can be appreciated based on the studies described above, the method of treatment based on a liposomal-prodrug of mitomycin C and a second agent provides for the synergistic treatment of a neoplasia in a subject in need of treatment. Neoplasias for which the treatment methods will be particularly useful include, without limitation, carcinomas, particularly those of the bladder, breast, cervix, colon, head and neck, melanoma, lung, ovary, pancreas, esophagus, and stomach. In a preferred embodiment of the invention, a method is provided for the synergistic treatment of breast, colon or colorectal, stomach, esophageal and pancreatic cancers. Advantageously, the synergistic method of the invention achieves beneficial effects including reducing the growth of tumors, reducing tumor burden, and/or producing tumor regression in a mammalian host. The method also prolongs survival of a tumor-bearing mammal.

In the methods of the present invention, a prodrug of mitomycin C is administered to a subject in combination with a second chemotherapeutic agent, such that a synergistic antineoplastic effect is produced. A "synergistic antineoplastic effect" refers to a greater-than-additive antineoplastic effect which is produced by a combination of the two drugs, and which exceeds that which would otherwise result from individual administration of either the prodrug alone, mitomycin C as a single agent alone, or the second chemotherapeutic agent alone. The data presented herein illustrates that a liposomal-mitomycin C prodrug administered in combination with paclitaxel, doxorubicin, or gemcitabine unexpectedly results in a synergistic antineoplastic effect by providing greater efficacy than would result from use of the agents alone. In some situations, liposomal-mitomycin C prodrug enhances the effect of paclitaxel, doxorubicin, or gemcitabine such that lower doses of one or both of the agents may be used in treating neoplasias, resulting in increased therapeutic efficacy and decreased side-effects.

One skilled in the art appreciates that a pharmaceutical composition comprising a combination of a prodrug of mitomycin C and a second chemotherapeutic agent can be administered to a subject by various routes including, for example, injection directly into a tumor, orally or parenterally, such as intravenously, intramuscularly, subcutaneously, intraorbitally, intranasally, intracapsularly, intraperitoneally, intracisternally, intra-tracheally, or intra-articularly. In a particular embodiment, the drugs are administered parenterally as a solution in normal saline.

Use of pharmaceutically acceptable carriers to administer the prodrug of mitomycin C and the second chemotherapeutic agent into dosages suitable for systemic administration is within the scope of the invention. With proper choice of carrier and suitable manufacturing practice, the prodrug of mitomycin C and the second chemotherapeutic agent may be administered parenterally, individually or in combination, such as by intravenous injection. Alternatively, one or both of the compounds can be formulated using pharmaceutically acceptable carriers well known in the art into dosages suitable for oral administration. Such carriers enable the prodrug of mitomycin C and/or the second chemotherapeutic agent to be formulated as tablets, pills, capsules, liquids, gels, syrups, slurries, suspensions and the like, for oral ingestion by a patient to be treated.

The actual dosage employed may be varied depending upon the requirements of the patient and the severity of the condition being treated. Determination of the proper dosage for a particular situation is within the skill of the art. In one embodiment, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired. Intermittent therapy (e.g., one week out of three weeks or three out of four weeks) may also be used.

Also, in accordance with the knowledge of the skilled clinician, the therapeutic protocols (e.g., dosage amounts and times of administration) can be varied in view of the observed effects of the administered therapeutic agents (i.e., antineoplastic agent(s) or radiation) on the patient, and in view of the observed responses of the disease to the administered therapeutic agents.

If formulated as a fixed dose, the active ingredients of the combination compositions of this invention are employed within predefined dosage ranges. For example, when 5-FU is used as the second chemotherapeutic agent it can be administered to humans at a dose in the range of 1-150 mg/kg/day, 5-75 mg/kg/day, or 10-50 mg/kg/day. By way of another example, an effective antineoplastic amount of paclitaxel administered intraperitoneally in humans can range from 60-120 mg/m$^2$, and administered intravenously may range from 50 to 200 mg/m$^2$, preferably from 80-175 mg/m$^2$.

When a liposomal-mitomycin C prodrug is administered in combination with at least one other agent, the at least one other agent can be co-administered in the same formulation. Alternatively, the various agents can be administered simultaneously (concurrently) in separate formulations. In addition, the agents can be administered in separate formulations, where the separate formulations are not administered simultaneously but are administered sequentially immediately with little or no time lapse between administration, or are administered sequentially during the same period of treatment, for example, during a daily or weekly period of treatment.

Accordingly, in the method of the present invention, administration of liposomal-mitomycin C prodrug "in combination with" a second chemotherapeutic agent refers to co-administration, which can intend administration concurrently, sequentially, or alternately. Concurrent administration refers to administration of both the liposomal-mitomycin C prodrug and the second chemotherapeutic agent at essentially the same time. Concurrent administration can be achieved via a single, combined formulation, containing both an amount of liposomal-mitomycin C prodrug that yields an effective amount of mitomycin C and an amount of the second chemotherapeutic agent in physical association with one another. The single, combined formulation may consist of a liquid mixture containing amounts of both liposomal-mitomycin C prodrug and second chemotherapeutic agent, which may be injected into the subject. It is also within the confines of the present methods that an amount of liposomal-mitomycin C prodrug and an amount of second chemotherapeutic agent be administered concurrently to a subject from separate, individual formulations. For example, the liposomal-mitomycin C prodrug can be administered via injection and the amount of second chemotherapeutic agent can be administered orally or via a different or same route of injection than that used for injection of the liposomal-mitomycin C prodrug.

In the methods described herein, liposomal-mitomycin C prodrug and the second chemotherapeutic agent also may be co-administered to a subject from separate, individual formulations that are spaced out over a period of time, so as to obtain the maximum efficacy of the combination. Administration of each drug may range in duration from a brief, rapid administration to a continuous perfusion. When spaced out over a period of time, co-administration of liposomal-mitomycin C prodrug and the second chemotherapeutic agent may be sequential or alternate. For sequential co-administration, one of the agents is separately administered, followed by the other. For example, a full course of treatment with liposomal-mitomycin C prodrug may be completed, and then may be followed by a full course of treatment with the second chemotherapeutic agent. Alternatively, for sequential co-administration, a full course of treatment with the second chemotherapeutic agent may be completed, then followed by a full course of treatment with liposomal-mitomycin C prodrug. For alternate co-administration, partial courses of treatment with liposomal-mitomycin C prodrug may be alternated with partial courses of treatment with the second chemotherapeutic agent, until a full treatment of each drug has been administered.

In another aspect, a kit or product for achieving the methods described herein is provided. The kit or product comprises a vial containing a prodrug of mitomycin C in an amount that yields a therapeutically-effective amount of mitomycin C; and instructions to administer the contents within the vial in combination with a chemotherapeutic agent. The kit may further comprise buffers, and other compositions to aid in administration to a host in need of treatment. The compositions may be formulated for specific dosing regimens. Each composition or solution may be contained in a vial or bottle and all components included in a box for commercial sale. The pharmaceutical compositions can be included in a container, pack, or dispensed together with instructional materials. The kits may comprise a single composition comprising both the liposomal-mitomycin C prodrug and second chemotherapeutic agent, or comprise separate containers with compositions of liposomal-mitomycin C prodrug and second chemotherapeutic agent.

III. Examples

The following examples are illustrative in nature and are in no way intended to be limiting.

EXAMPLE 1

Liposomal Mitomycin C Prodrug Preparation

A prodrug conjugate of mitomycin C releasably attached to a lipophilic moiety, para-diacyldiglyceroldithiobenzal-mitomycin C, was synthesized as described in U.S. Pat. No. 7,303,760, in Example 2, incorporated by reference herein.

The para-diacyldiglyceroldithiobenzal-mitomycin C prodrug conjugate was incorporated into a liposomal delivery vehicle as described in Example 3A of U.S. Pat. No. 7,303,760, incorporated by reference herein.

EXAMPLE 2

Toxicity of the Prodrug Alone and in Combination with Co-Administered Chemotherapeutic Agents Prodrug conjugate of mitomycin C was prepared and incorporated into a liposome delivery platform as described in Example 1. The prodrug conjugate incorporated into a liposome delivery platform is referred to as "liposomal-mitomycin C prodrug."

Twenty BALB/c mice were randomly separated into four treatment groups of five mice each, named Groups 1-4, for treatment as follows:

Group 1: liposomal-mitomycin C prodrug (PROMITIL®), 45 mg/kg via intravenous (iv) injection once per day on study days 1 and 8;

Group 2: liposomal-mitomycin C prodrug, 30 mg/kg via iv injection once daily on study days 1 and 8 and liposome-entrapped doxorubicin (DOXIL®), 8 mg/kg via iv injection, once daily on study days 1 and 8, where the two agents were injected concurrently;

Group 3: liposomal-mitomycin C prodrug, 30 mg/kg via iv injection once daily on study days 1 and 8 and paclitaxel (TAXOL®), 10 mg/kg via intraperitoneal (ip) injection once daily on study days 1, 3, 5, 8, 10, and 12; and Group 4: liposomal-mitomycin C prodrug, 30 mg/kg via iv injection once per day on study days 1 and 8 and gemcitabine (GEMZAR®) 100 mg/kg via iv injection once per day on study days 1, 4, 8, and 11.

The mice were observed for 100 days, and the results are shown in FIG. 1, where Group 1 corresponds to the line filled with solid diamonds; Group 2 corresponds to the line filled with diagonal stripes; Group 3 corresponds to the line filled with the dashed horizontal lines; and Group 4 corresponds to the line with solid fill. Treatment with liposomal-mitomycin C prodrug in combination with paclitaxel (Group 3, line with dashed horizontal fill) resulted in an acute 20% toxic death rate and treatment with liposomal-mitomycin C prodrug at the 45 mg/kg dose resulted in a 20% toxic death observed at about day 90 of the study. The animals treated with a combined treatment of liposomal-mitomycin C prodrug and gemcitabine (Group 4, solid line in FIG. 1) had no toxic deaths.

EXAMPLE 3

Toxicity of the Prodrug Alone and in Combination with Co-Administered Chemotherapeutic Agents A prodrug of mitomycin C was prepared and incorporated into a liposome delivery platform as described in Example 1. The prodrug conjugate incorporated into a liposome delivery platform is referred to as "liposomal-mitomycin C prodrug."

Twenty BALB/c mice were randomly separated into four treatment groups of five mice each, named Groups 1-4, for treatment as follows:

Group 1: liposomal-mitomycin C prodrug (PROMITIL®), 30 mg/kg via iv injection once per day on study days 1 and 8;

Group 2: liposomal-mitomycin C prodrug, 20 mg/kg via iv injection once daily on study days 1 and 8 and liposome-entrapped doxorubicin (DOXIL®), 8 mg/kg via iv injection, once daily on study days 1 and 8;

Group 3: liposomal-mitomycin C prodrug, 20 mg/kg via iv injection once daily on study days 1 and 8 and paclitaxel (TAXOL®), 10 mg/kg, via intraperitoneal (ip) injection once daily on study days 1, 3, 5, 8, 10, and 12; and Group 4: liposomal-mitomycin C prodrug, 20 mg/kg via iv injection once per day on study days 1 and 8 and gemcitabine (GEMZAR®) 100 mg/kg via iv injection once per day on study days 1, 4, 8, and 11.

The mice were observed for 100 days, and the results are shown in FIG. 2, where results for the Group 1 animals corresponds to the line with solid fill; Group 2 corresponds to the line filled with diagonal stripes; Group 3 corresponds to the line with dashed horizontal fill; and Group 4 corresponds to the line filled with solid diamonds. Treatment with liposomal-mitomycin C prodrug at a dose of 30 mg/kg resulted in no toxic deaths. Liposomal-mitomycin C prodrug at a dose of 30 mg/kg in combination with paclitaxel (Group 3, line with dashed horizontal fill), with liposome-entrapped doxorubicin (Group 2; line with diagonal stripes fill), or with gemcitabine (Group 4, line filled with solid diamonds) each resulted in 20% toxic deaths.

EXAMPLE 4

Dosing Sequence

Four mice were treated via iv injection with liposome-entrapped doxorubicin at a dose of 8 mg/kg and after 48 hours with liposomal-mitomycin C prodrug (prepared according to Example 1) via iv injection at a dose of 30 mg/kg. Another group of 4 animals was treated first with liposomal-mitomycin C prodrug via iv injection at a dose of 30 mg/kg and after 48 hours with liposome-entrapped doxorubicin at a dose of 8 mg/kg.

Over the observation period following treatment with the chemotherapeutic agents, there was reduction of the weight in both groups. One mouse died at the group that was treated first with liposomal-mitomycin C prodrug. No other deaths were observed. According to the weight results there was no substantial difference in toxicity between the two different treatments.

EXAMPLE 5

Pharmacokinetics

A prodrug of mitomycin C was prepared and incorporated into a liposome delivery platform as described in Example 1. BALB/c mice were randomly separated into two treatment groups of three mice each for treatment as follows:

Group 1: liposomal-mitomycin C prodrug (PROMITIL®), 30 mg/kg via iv injection (n=3);

Group 2: liposome-entrapped doxorubicin (DOXIL®), 5 mg/kg via iv injection (n=3); and Group 3: liposomal-mitomycin C prodrug (PROMITIL®), 30 mg/kg via iv injection and liposome-entrapped doxorubicin (DOXIL®), 5 mg/kg via iv injection (n=8).

Blood was collected and mice were sacrificed after 1 hour and 24 hours. Concentration of liposome-entrapped doxorubicin was determined by fluorescence and the concentration of liposomal-mitomycin C prodrug was determined by HPLC analysis. The results are shown in FIGS. 3A-3B. According to the results the rate of liposome-entrapped doxorubicin clearance is slower than that of liposomal-mitomycin C prodrug and there was no change in the clearance when both the prodrug and liposome-entrapped doxorubicin were co-injected.

EXAMPLE 6

Anti-Tumor Effect in Colon Carcinoma Tumor Model

A prodrug of mitomycin C was prepared and incorporated into a liposome delivery platform as described in Example 1. C26 (colon carcinoma) mouse tumor model was used by injecting BALB/c F intraperitoneally with 1 million tumor cells. The day of ip injection with tumor cells was defined as study day zero. The mice were randomized into groups for treatment as follows:

Group 1: control, untreated;

Group 2: liposome-entrapped doxorubicin (DOXIL®), 5 mg/kg via iv injection on study days 5 and 12;

Group 3: liposomal-mitomycin C prodrug (PROMITIL®), 30 mg/kg via iv injection on study days 5 and 12;

Group 4: liposomal-mitomycin C prodrug (PROMITIL®), 30 mg/kg via iv injection and liposome-entrapped doxorubicin (DOXIL®), 5 mg/kg via iv injection, both agents injected concurrently on study days 5 and 12;

Group 5: liposomal-mitomycin C prodrug (PROMITIL®), 30 mg/kg via iv injection and gemcitabine, 100 mg/kg via ip injection, both agents administered on study days 5, 8, 12, and 15;

Group 6: liposomal-mitomycin C prodrug (PROMITIL®), 30 mg/kg via iv injection and paclitaxel, 15 mg/kg via ip injection, both agents administered on study days 5, 8, 12, and 15;

Group 7: gemcitabine (GEMZAR®), 100 mg/kg, via ip injection, on study days 5, 8, 12, and 15; and Group 8: paclitaxel (TAXOL®), 15 mg/kg via ip injection, on study days 5, 8, 12, and 15.

The animals were observed for 45 days, and percent survival recorded. Results are shown in FIGS. 4A-4B, where results for all study groups are shown in FIG. 4A and results for Group 1 (control, untreated), Group 2 (liposome-entrapped doxorubicin), Group 3 (liposomal-mitomycin C prodrug) and Group 4 (liposomal-mitomycin C prodrug in combination with liposome-entrapped doxorubicin) are shown in detail in FIG. 4B.

EXAMPLE 7

Anti-Tumor Effect in Gastric Tumor Model

A prodrug of mitomycin C was prepared and incorporated into a liposome delivery platform as described in Example 1. An N87 human gastric tumor model was selected, and established by inoculating $10^6$ N87 tumor cells into the footpad of nude mice via subcutaneous (sc) injection. The day of sc injection with tumor cells was defined as study day zero. The mice were randomized into groups for treatment as follows:

Group 1: control, placebo liposomes administered via iv injection on study days 5 and 12;

Group 2: liposome-entrapped doxorubicin (DOXIL®), 5 mg/kg via iv injection on study days 5 and 12;

Group 3: liposomal-mitomycin C prodrug (PROMITIL®), 25 mg/kg via iv injection on study days 5 and 12;

Group 4: liposomal-mitomycin C prodrug (PROMITIL®), 25 mg/kg via iv injection and liposome-entrapped doxorubicin (DOXIL®), 5 mg/kg via iv injection, both agents injected on study days 5 and 12;

Group 5: paclitaxel (TAXOL®), 15 mg/kg via ip injection, on study days 5, 8, 12, and 15; and Group 6: liposomal-mitomycin C prodrug (PROMITIL®), 25 mg/kg via iv injection on study days 5 and 12, and paclitaxel, 15 mg/kg via ip injection, on study days 5, 8, 12, and 15.

The animals were observed for 50 days, and survival and tumor size were recorded. FIGS. 5A-5B shows the results for the percent of animals with a tumor volume less than 5 mm surviving as a function of days post tumor inoculation, and FIGS. 5C-5H show the tumor volume of each animal in the test groups as a function of days post tumor inoculation. The survival results show that the combination of liposomal-mitomycin C prodrug and paclitaxel is statistically significantly more effective than liposomal-mitomycin C prodrug alone and is also statistically significantly more effective than paclitaxel alone. The combination of liposomal-mitomycin C prodrug in combination with liposome-entrapped doxorubicin was more effective in inhibiting tumor growth than liposomal-mitomycin C prodrug alone and was more effective in inhibiting tumor growth than liposome-entrapped doxorubicin alone.

EXAMPLE 8

Anti-Tumor Effect in Melanoma Tumor Model

A prodrug of mitomycin C was prepared and incorporated into a liposome delivery platform as described in Example 1. A human A375 melanoma subcutaneous tumor model was selected, and established by inoculating tumor cells into nude mice via subcutaneous (sc) injection. The day of sc injection with tumor cells was defined as study day zero. The mice were randomized into groups for treatment as follows:

Group 1: control, untreated;

Group 2: liposomal-mitomycin C prodrug (PROMITIL®), 25 mg/kg via iv injection on study days 11 and 18;

Group 3: paclitaxel (TAXOL®), 15 mg/kg via ip injection, on study days 11, 14, 18 and 21; and Group 4: liposomal-mitomycin C prodrug (PROMITIL®), 25 mg/kg via iv injection and paclitaxel (TAXOL®), 15 mg/kg via ip injection, both agents injected on study days 11, 18 and 11, 14, 18 and 21.

The tumor size of the animals (n=6) in each treatment group was measured, and the median tumor size (in mm) is shown in FIG. 6 as a function of days post tumor inoculation. The data show the combination of liposomal-mitomycin C prodrug and paclitaxel was more effective in tumor growth inhibition than liposomal-mitomycin C prodrug alone.

EXAMPLE 9

Anti-Tumor Effect in Breast Cancer Model

A prodrug of mitomycin C was prepared and incorporated into a liposome delivery platform as described in Example 1. A subcutaneous 4T1 breast mouse tumor model was selected, and established by inoculating tumor cells subcutaneously into BALB/c f mice. The day of sc injection with tumor cells was defined as study day zero. The mice were randomized into groups for treatment as follows:

Group 1: control, untreated;

Group 2: mitomycin C as a free drug (not a prodrug), 6 mg/kg via iv injection on study day 5;

Group 3: liposome-entrapped doxorubicin (DOXIL®), 10 mg/kg via iv injection, on study day 5;

Group 4: liposomal-mitomycin C prodrug (PROMITIL®), 40 mg/kg via iv injection on study day 5;

Group 5: mitomycin C as a free drug (not a prodrug), 4 mg/kg via iv injection and liposome-entrapped doxorubicin (DOXIL®), 8 mg/kg via iv injection, both drugs administered on study day 5; and Group 6: liposomal-mitomycin C prodrug (PROMITIL®), 30 mg/kg via iv injection and liposome-entrapped doxorubicin (DOXIL®), 8 mg/kg via iv injection, both agents injected on study day 5.

The tumor size of the animals in each treatment group was measured, and the median tumor size (in mm) is shown in FIG. 7 as a function of days post tumor inoculation. The data shows the combination of liposomal-mitomycin C prodrug and liposome-entrapped doxorubicin (Group 6) was more effective in inhibiting tumor growth than liposomal-mitomycin C prodrug alone or liposome-entrapped doxorubicin alone, and was also superior than the combination of mitomycin C and liposome-entrapped doxorubicin.

EXAMPLE 10

Anti-Tumor Effect in Gastric Tumor Model

A prodrug of mitomycin C was prepared and incorporated into a liposome delivery platform as described in Example 1. An N87 human gastric tumor model was selected, and established by inoculating N87 tumor cells into the footpad of nude mice via subcutaneous (sc) injection. The day of sc injection with tumor cells was defined as study day zero. The mice were randomized into groups for treatment as follows:
Group 1: control, untreated;
Group 2: mitomycin C as a free drug (not a prodrug), 5 mg/kg via iv injection on study days 6 and 13;
Group 3: liposomal-mitomycin C prodrug (PROMITIL®), 35 mg/kg via iv injection on study days 6, and 13;
Group 4: paclitaxel (TAXOL®), 15 mg/kg via ip injection, on study days 6, 10, 13 and 17;
Group 5: mitomycin C as a free drug (not a prodrug), 5 mg/kg via iv injection on study days 6 and 13; and paclitaxel (TAXOL®), 15 mg/kg via ip injection, on study days 6, 10, 13 and 17; and
Group 6: liposomal-mitomycin C prodrug (PROMITIL®), 35 mg/kg via iv injection on study days 6 and 13 and paclitaxel (TAXOL®), 15 mg/kg via ip injection, on study days 6, 10, 13 and 17.

The tumor size of the animals in each treatment group was measured. The results obtained showed that the combination of liposomal-mitomycin C prodrug and paclitaxel was more effective in inhibiting tumor growth than liposomal-mitomycin C prodrug alone and was more effective in inhibiting tumor growth than paclitaxel alone. Although initial observations suggested the combination therapy of liposomal-mitomycin C prodrug and paclitaxel was not superior to the combination of free mitomycin C and paclitaxel, inspection of the data shows that treatment with free mitomycin C and paclitaxel in combination was toxic to the animals, as evidenced by two deaths in the treatment group and weight loss of greater than 20%. Evaluation of the data after removing those mice with unacceptable toxicity (toxic deaths and drop >20% of weight) is presented in FIG. 8. The data in FIG. 8 shows the severe toxicity of the combined treatment of free mitomycin C and paclitaxel. The data also shows that of the treatment regimens, the only treatment safe and effective was the combination of liposomal-mitomycin C prodrug and paclitaxel.

EXAMPLE 11

Anti-Tumor Effect of Prodrug and 5-Fluorouracil

Mice (BALB/c F) with a C26 (colon carcinoma) tumor model are obtained by injecting intraperitoneally with 1 million tumor cells. The mice are randomized into groups for treatment with mitomycin C as a free agent, liposomal-mitomycin C prodrug (prepared according to Example 1), 5-fluorouracil (5-FU), a combination of mitomycin C (as a free agent) and 5-FU, or a combination of liposomal-mitomycin C prodrug and 5-FU. One group of mice is left untreated for a control. The designated treatment agent(s) is/are injected 5 days and 10 days after tumor inoculation with extra-injections of 5-FU on days 8 and 13, and the animals are observed for up to 60 days, and percent survival and clinical signs recorded. Animals treated with liposomal-mitomycin C prodrug in combination with 5-FU have improved percent survival indicating a greater inhibition of tumor growth compared to animals treated with the single agents or with a combination of mitomycin C and 5-FU.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

It is claimed:
1. A treatment method, comprising:
administering to a subject in need a prodrug of mitomycin C in an amount that yields a therapeutically-effective amount of mitomycin C, wherein the prodrug is a conjugate of mitomycin C releasably attached to a lipophilic moiety, and is of the form:

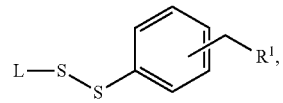

wherein L is a hydrophobic moiety, $R^1$ represents a mitomycin C residue, the —$CH^2R^1$ group is selected from the ortho position and the para position; and
administering in combination with the prodrug a chemotherapeutic agent.
2. The method of claim 1, wherein the providing a prodrug of mitomycin C comprises providing via injection a prodrug of mitomycin C.
3. The method of claim 2, wherein the providing via injection comprises intravenous, intraarterial, intraperitoneal, intrapleural, intrathecal, intravesical or intratumoral injection.
4. The method of claim 1, wherein instructing comprises instructing to administer the chemotherapeutic agent concurrently or sequentially with the prodrug.
5. The method of claim 1, wherein the chemotherapeutic agent is a liposome-entrapped chemotherapeutic agent.
6. The method of claim 5, wherein the chemotherapeutic agent is doxorubicin or daunorubicin.
7. The method of claim 1, wherein the chemotherapeutic agent is a taxane.
8. The method of claim 7, wherein the taxane is selected from paclitaxel and docetaxel.
9. The method of claim 5, wherein the chemotherapeutic agent is gemcitabine.
10. The method of claim 5, wherein the chemotherapeutic agent is a fluoropyrimidine.
11. The method of claim 10, wherein the fluopyrimidine is 5-fluorouracil or a prodrug of 5-fluorouracil.
12. The method of claim 11, wherein the prodrug of 5-fluorouracil is capecitabine.
13. The method of claim 1, wherein instructing comprises instructing to administer the chemotherapeutic agent orally.
14. A treatment method for a subject with cancer, comprising:
administering a prodrug of mitomycin C in an amount that yields a therapeutically-effective amount of mitomycin C, wherein the prodrug is a conjugate of mitomycin C releasably attached to a lipophilic moiety, and is of the form:

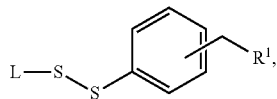

wherein L is a hydrophobic moiety, R¹ represents a mitomycin C residue, the —CH₂R¹ group is selected from the ortho position and the para position; and administering a chemotherapeutic agent;

whereby by said administering steps provide a reduction in tumor volume or prolong survival of the subject, when compared to that achieved by administering the prodrug or the chemotherapeutic agent alone.

15. The method of claim 1, wherein administering the chemotherapeutic agent comprises administering concurrently or sequentially with administering the prodrug.

16. The method of claim 14, wherein the chemotherapeutic agent is a liposome-entrapped chemotherapeutic agent.

17. The method of claim 16, wherein the chemotherapeutic agent is doxorubicin or daunorubicin.

18. The method of claim 14, wherein the chemotherapeutic agent is a taxane.

19. The method of claim 14, wherein the cancer is breast cancer, colon cancer, colorectal cancer, stomach cancer, esophageal cancer, pancreatic cancer, melanoma, or bladder cancer.

20. A method for treating a solid tumor, comprising:

administering a prodrug of mitomycin C in an amount that yields a therapeutically-effective amount of mitomycin C, wherein the prodrug is a conjugate of mitomycin C releasably attached to a lipophilic moiety, and is of the form:

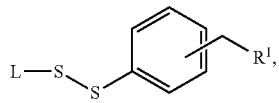

wherein L is a hydrophobic moiety, R¹ represents a mitomycin C residue, the —CH₂R¹ group is selected from the ortho position and the para position; and administering in combination with the prodrug a chemotherapeutic agent.

21. The method of claim 20, wherein the chemotherapeutic agent is a liposome-entrapped chemotherapeutic agent.

22. The method of claim 21, wherein the chemotherapeutic agent is a taxane.

* * * * *